United States Patent [19]

Short et al.

[11] Patent Number: 5,510,099

[45] Date of Patent: * Apr. 23, 1996

[54] MUTAGENESIS TESTING USING TRANSGENIC NON-HUMAN ANIMALS CARRYING TEST DNA SEQUENCES

[75] Inventors: Jay M. Short, Encinitas; Patricia L. Kretz, San Marcos, both of Calif.

[73] Assignee: Stratagene, La Jolla, Calif.

[*] Notice: The portion of the term of this patent subsequent to Sep. 13, 2011, has been disclaimed.

[21] Appl. No.: 125,618

[22] Filed: Sep. 23, 1993

Related U.S. Application Data

[63] Continuation of Ser. No. 837,031, Feb. 14, 1992, abandoned, which is a continuation-in-part of Ser. No. 505,676, Apr. 5, 1990, abandoned, which is a continuation-in-part of Ser. No. 45,037, May 1, 1987, abandoned.

[51] Int. Cl.$^6$ ............................ A61K 49/00; C12N 15/00
[52] U.S. Cl. .............................. 424/9.2; 424/9.1; 800/2; 800/DIG. 1; 435/172.3; 435/320.1; 435/317.1; 935/31; 935/72; 935/73; 935/111
[58] Field of Search .................................... 800/2, DIG. 1; 424/2, 9; 435/172.3, 320.1, 317.1; 935/31, 72, 73, 77, 111

[56] References Cited

U.S. PATENT DOCUMENTS 5,347,075  9/1994  Sorge .......................................... 800/2

OTHER PUBLICATIONS

Ptashne, "A Genetic Switch: Gene Control and Phage Lambda", Blackwell Scientific Publ., Inc. Palo Alto, Calif. (1986).
Gossen et al., Nucleic Acids Res. 16(19):9343 (1988).
Raleigh et al., Nucleic Acids Res. 16(4):1563–1575 (1988).
Bickle, "Nucleases", pp. 85–108, Linn et al. eds., Cold Spring Harbor Laboratory, Cold Spring Harbor, N.Y. (1985).
Heitman et al., J. Bacteriol., 169:3243–3250 (1987).
Herrero et al., J. Bacteriol., 172:6557–6567 (1990).
Raleigh et al., Proc. Natl. Acad. Sci. USA, 83:9070–9074 (1986).
Ross et al., J. Bacteriol., 171:1974–1981 (1989).

Primary Examiner—Jasemine C. Chambers
Attorney, Agent, or Firm—Pennie & Edmonds

[57] ABSTRACT

An assay for monitoring and assessing the mutagenic potential of agents which involves creating transgenic non-human animals carrying a test DNA sequence or sequences that can be quickly recovered and examined for mutations following exposure to one or more suspected mutagenic agents.

13 Claims, 7 Drawing Sheets

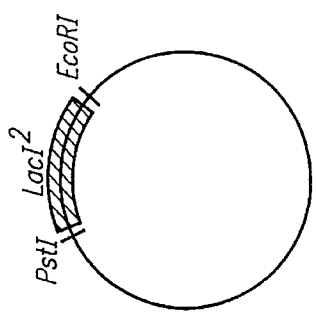
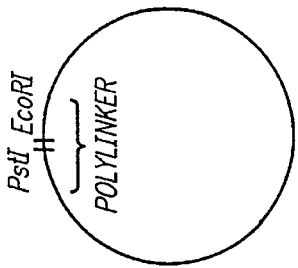
FIG. 5
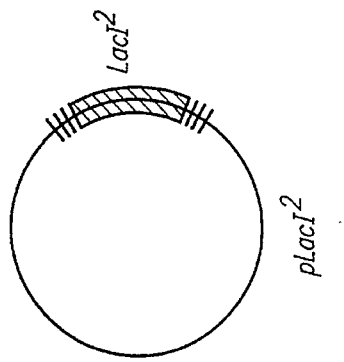
FIG. 4
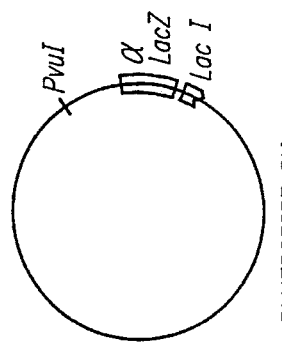
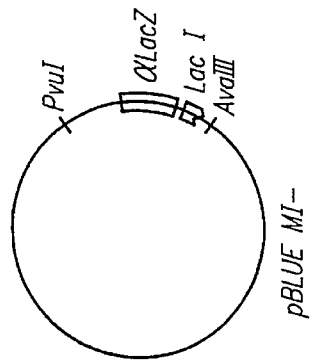

MUTAGENESIS TESTING USING TRANSGENIC NON-HUMAN ANIMALS CARRYING TEST DNA SEQUENCES

CROSS REFERENCE TO RELATED APPLICATIONS

This application is a continuation of application Ser. No. 07/837,031, filed Feb. 14, 1992, now abandoned which is a continuation-in-part application of U.S. patent application Ser. No. 505,676, filed Apr. 5, 1990 now abandoned, which is a continuation-in-part of U.S. patent application Ser. No. 045,037, filed May 1, 1987 now abandoned for "Hutagenesis Testing Using Transgenic Non-Human Animals Carrying Test DNA Sequences," the disclosures of which are specifically incorporated herein by reference.

TECHNICAL FIELD

This invention relates to transgenic animals and to tests for monitoring mutagenic agents in live animals. More specifically, this invention relates to the creation of transgenic non-human animals carrying test DNA sequences and to methods for monitoring and assessing the mutagenic potential of agents by exposing the transgenic animal to one or more suspected mutagens, and optionally recovering the test DNA sequence, and examining the test DNA sequence for mutations. Novel methods for increasing the efficiency of test DNA sequence recovery and rapid analysis of specific test DNA mutations are also described.

BACKGROUND

Various agents, such as radiation, ultraviolet light, synthetic chemicals, natural substances, and aberrations in genetic replication and repair can produce mutations in DNA. The results of a representative study indicate that as many as 60% of the cancers that develop in women and as many as 40% of those that develop in men result from avoidable exposure to mutagens from dietary intake. Vuoto et al., *Environ. Mutaqen,* 7:577–598 (1985). Exposure to environmental mutagens such as nitroaromatic compounds found in automobile exhaust, chlorination by-products used in drinking water, and acrylamide and formaldehyde used extensively in industrial laboratories is also of major concern. Quantitative measurement of the effect of suspected mutagens is essential to control exposure to harmful agents. Additionally, whenever a new chemical, drug, or food additive, for example, is to be taken from the laboratory to the marketplace, it must be tested for its toxicity and cancer-causing potential. As a result, significant effort has gone into the development of assays that detect the mutagenic potential of various compounds.

Existing tests that assess the mutagenic potential of substances focus either on alterations of DNA in cultured cells or bacteria or alterations in the health of test animals. However, few tests that monitor alterations in DNA actually expose live animals to the agent to be tested. This is because it is very difficult to rapidly monitor alterations in the genetic code simultaneously in many different organs. Tests to detect these mutations must be very sensitive. They must be able to detect a single mutation amongst millions of normal genetic units. The difficulty of this task currently makes this approach for live animal studies prohibitively expensive as well as time intensive. Therefore, most current live animal genotoxicity tests use disease formation or large scale chromosomal alterations as an assay for gene alteration.

The problem of readily detecting small scale DNA alterations that are caused by potential mutagenic agents has generally been approached by performing studies on procaryotic or eukaryotic cells in culture (in vitro tests). The well-known Ames' test uses a special strain of bacteria to detect these mutations. Ames, et al., An Improved Bacterial Test System for the Detection and Classification of Mutagens and Carcinogens, *Proc. Nat. Acad. Sci.,* 70:782–86 (1973). This test and many analogues that use other types of bacterial or animal cells permit the rapid screening of very large numbers of cells for the appearance of an altered phenotype. The appearance of this altered phenotypic trait reflects the occurrence of a mutation within the test gene. These tests are, however, insensitive to or nonspecific for many mutagens that result from metabolic activation of the agent being screened. Although attempts have been made to increase their sensitivity and specificity by activation of such metabolites with liver and other extracts it is noted that, for instance, the metabolites produced by these extracts are often not present at the same concentrations as in the live tissues of an animal. Metabolites that are only produced in other organs are not detected at all.

Eukaryotic cell lines have also been used to detect mutations. E.g., Glazer et al., Detection and Analysis of UV-induced Mutations in Mammalian Cell DNA using Lambda Phage Shuttle Vector, *Proc. Natl. Acad. Sci. USA,* 83:1041–1044 (1986). In this test a target test gene, the amber suppressor tyrosine tRNA gene of *E. coli* in a bacteriophage shuttle vector, was integrated into a genomic host mammalian cell line by DNA transfection of cultured cells in vitro. After exposing the host cell line to putative mutagenic agents, test genes were reisolated, propagated in bacteria, and analyzed for mutations. Because the host is only a mammalian cell line and not a live animal, the test is incapable of accurately monitoring mutagenic metabolites of the agent being tested that are only produced at the appropriate concentrations by differentiated cells or the tissue of live animals.

A two year study by the NIH concluded that data obtained from four different prokaryotic and eukaryotic in vitro assays had only a 60% concordance with whole animal carcinogenicity studies. Tennant et al., *Science,* 236:933–941 (1987). The study suggests that the high rate of error may result from potential variation in genetic susceptibility between in vitro systems and whole animals. For example, metabolites, frequently involved in activation of promutagens, are not present in in vitro systems, allowing mutagenic potential to go undetected. In addition, differences in DNA repair mechanisms between prokaryotes and eukaryotes may account for some discrepancies in results.

Test genes and large scale screening assays used for in vitro assays are not available for live animal studies. Short of relying on long term animal studies that detect phenotypic changes that require a long time to be identifiable, such as tumors, organ failure, coat color, etc., current tests do not provide a means for monitoring organ-specific mutations of DNA. Hence, there exists a need for a system that places a test DNA sequence within an animal and is subsequently assayed on a large scale for mutations. There also exists a need for methods that detect mutations caused by chemical metabolites of the agent being tested. To be most effective the system needs to be capable of monitoring genetic changes in as many tissues of an animal and as easily, rapidly, and inexpensively as possible.

The present invention, providing novel transgenic non-human mammals and methods utilizing such mammals for mutagenesis testing, satisfies these needs. More specifically, the present invention provides a sensitive screen for the mutagenicity of suspected agents and permits the monitoring of the mutagenic effects of such agents and the mutagenic effects of the metabolites of such agents. Additionally, the invention can permit the identification of the nature of the mutation, e.g., DNA transition, transversion, deletion, or a point or frameshift mutation. Further, the methods of the invention offer the significant advantage of being rapid to perform, thus permitting the identification of potential mutagens appreciably before other tests can be completed, and is inexpensive relative to other whole animal tests. And, the present invention substantially reduces the number of animals which must be used for mutagenesis testing.

SUMMARY OF THE INVENTION

The present invention contemplates a method for assaying the mutagenic potential of an agent. The method comprises administering a predetermined amount of the agent to an animal containing cells having a genome characterized by the presence of an excisably-integrated lambda phage. The phage contains a target gene operatively linked to prokaryotic expression signals. The exposed animal is typically maintained alive for a predetermined period of time, usually from hours to months, and preferably from days to weeks, such as about 4 days to two weeks. A predetermined amount of the excisably-integrated lambda phage is then rescued from cells harvested from the maintained animal. The rescued lambda phage is then introduced into and expressed in a restriction system deficient microorganism.

In a preferred embodiment, the animal is a transgenic animal, such as a transgenic rodent, preferably a transgenic rat or mouse.

In another preferred embodiment, the cells are human cells present in a SCID mouse.

As described below, a preferred method has been developed which uses a target gene system comprised of a set of two genes, a test gene and a reporter gene, incorporated into animals or animal cells to screen for compounds having mutagenic, carcinogenic or teratogenic activity. Exposure of the animals or animal cells to compounds having any of these activities causes mutations resulting in alterations in expression of the reporter gene. Both the target gene and the reporter gene constructs are operatively linked to a prokaryotic promoter.

This method has several advantages over the prior art methods of screening for compounds having mutagenic or teratogenic activity. The most significant advantage is the ease in detection and decrease in number of false positives. Although the mutation of genes encoding reporter proteins has previously been used to assay for mutagenic activity, the mutational event resulted in the protein not being expressed. Detecting a single cell, or even a few cells, not expressing a protein, while surrounded by cells which express the protein, is difficult, tedious, and subject to a high percentage of error. In contrast, in the present method, the mutational event ultimately results in the expression of a reporter molecule which would otherwise not be expressed, and which is readily detected.

As used herein, unless specifically stated otherwise, "animal cells" will be used to include cells in cell cultures, embryos, and differentiated animals. As also used herein, "mutagen" will be used to include toxins, carcinogens, teratogens, and other agents which alter DNA or RNA sequence or expression, unless stated otherwise.

The selection of reporter genes is based on the following criteria: (i) the reporter gene product cannot be detrimental or lethal to the transformed cells, (ii) the gene product should provide a simple and sensitive detection system for its quantitation, and (ii) non-transformed cells should have a low constitutive background of gene products or activities that will be assayed. Reporter genes which encode enzymes; antigens or other biologically active proteins which can be monitored easily by biochemical techniques are preferred. These include beta-galactosidase (Norton, P. A. and Coffin, J. M., *Mol. Cell. Biol*, 5:281–290 (1985), peroxidase and luciferase (de Wet, J. R. et al., *Mol. Cell. Biol*, 7:725–737 (1987).

The test gene is selected from the group of sequences which encode regulatory molecules that bind to a sequence controlling reporter gene expression. These can be repressors or other regulatory molecules, including anti-sense RNA. In the most preferred embodiment, the lacI repressor gene is used as a mutagenesis target. The inactivation of the repressor gene by a mutagenic even causes the transcription and translation of a defective repressor protein that is no longer able to repress expression of the reporter gene the lacz gene encoding beta-galactosidase. Alteration of the operator region for the reporter gene in a manner that prevents binding of the repressor protein produces the same effect. Derepression of the reporter gene can then be monitored by assaying for defined functions of the gene product.

The bacterial lac operator-repressor system is preferred because it is one of the most basic and thoroughly studies examples of a protein-nucleic acid interaction that regulates transcription of a gene, as described by Coulondre and Miller, *Mol. Biol.*, 117:577 (1977) and Miller, *Ann. Rev. Genet.*, 17:215 (1983). This bacterial regulatory system has been transfected into mammalian cells and expression detected by addition of an inducer, isopropyl beta-D thiogalactoside (IPTG), as reported by Hu and Davidson, *Cell*, 48:555 (1987), and Brown, et al., *Cell*, 49:603 (1987). An important difference between previous uses of the lac operator-repressor system and the present method is that mutation rather than induction is used to derepress the reporter genes to express protein whose function is solely to serve as an indicator. Another difference is that, in the preferred embodiment, the target gene system is excisable as an infectious lambda phage.

For the repressor protein to control the expression of a reporter gene, the operator sequence has to be built into the reporter gene at the location between the transcription initiation site and the initiation codon ATG. Either an original lac operator sequence (5'-GGAATTGTGAGCG-GATAACAATCC-3'), [SEQ ID NO: 3] or a mutant lac operator (lacIq), for example, a sequence which binds repressor eight time tighter (5'-ATTGTGAGCGCTCA-CAAT-3'), [SEQ ID NO: 2] can be used in vector construction.

Figure 1:
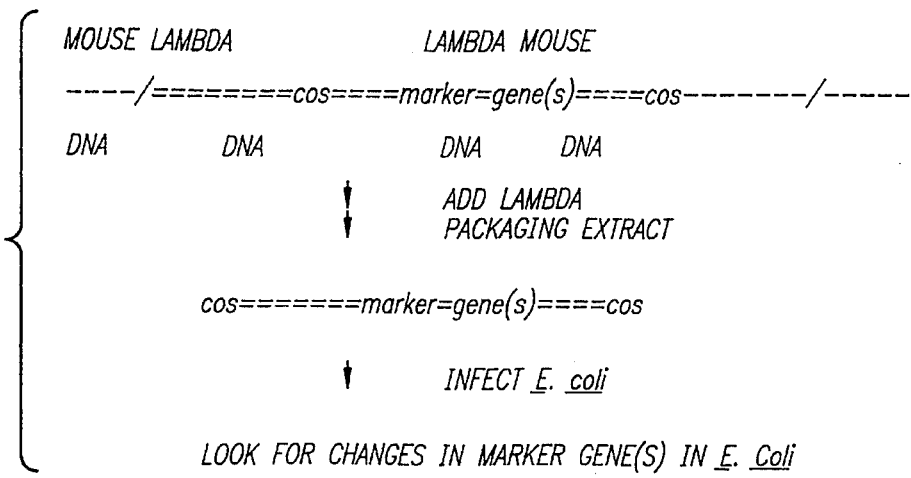
FIG. 1

This figure provides a diagram of the method of the invention.

FIG. 2

This drawing provides a schematic diagram for a method for detecting changes in marker genes.

FIG. 3

This drawing provides a restriction map of several different plasmids that may be used in the subject invention.

FIG. 4

This drawing provides a schematic diagram of the construction of plasmid pBlueMI⁻.

FIG. 5

This drawing provides a schematic diagram of the construction of plasmid pLacI$^q$.

FIG. 6

This drawing provides a schematic diagram of the construction of plasmid pInt.1.

FIG. 7

This drawing provides a schematic diagram of the construction of plasmid pPrelacIqZ.

FIG. 8

This drawing provides a schematic diagram of the construction of lambda LIZ Alpha.

FIG. 9

This drawing is a graph of mutagenesis frequency data obtained through the use of transgenic mice.

DETAILED DESCRIPTION OF THE INVENTION

The present invention contemplates engineered animal cells, animal embryos and differentiated animals having a genome characterized by the presence of an excisably-integrated lambda phage containing a target gene system. The target gene system comprises a test gene (transcribable, and preferably translatable DNA sequence). Preferably, the test gene is operatively linked to prokaryotic expression signals, such as a promoter, ribosome binding site, stop codon, and the like.

An rDNA of this invention (subject rDNA) contains a target gene system operatively link for prokaryotic expression to a lambda phage. A target gene system typically is operatively linked to a lambda phage and can be comprised of any of a variety of test genes whose transcription results in a detectable phenotype or genotype where a mutation in the nucleotide sequence of a test gene measurably alters the detectable phenotype or genotype. Typical test genes include genes that confer drug resistance or other selective advantage, or genes whose expression alters the expression of a second reporter gene. Exemplary drug resistance genes confer resistance to ampicillin, kanamycin, chloramphenicol and the like.

A preferred test gene is a repressor or activator gene product whose expression directly alters the expression of a reporter gene. Exemplary is the repressor protein encoded by the lacI gene, and genetic variants of the lacI gene that function to block transcription of the beta-galatosidase gene (lacZ) by binding to the operator region of the lacZ gene's expression signals. In this system, lacZ is a reporter gene. A preferred lacI gene is the lacIq variant that expresses eight- to ten-fold elevated levels of repressor protein and more tightly represses expression of the lacZ gene.

In preferred embodiments, the test gene of the target gene system is operatively linked to a reporter gene.

A reporter gene provides a means for detecting mutations in the test gene. Typical reporter genes are expressed when the test gene is not mutated, and are not expressed when the test gene is expressed. Thus a reporter gene is a gene that encodes a detectable phenotype or genotype and whose expression is under the control of the test gene.

Genes that encode detectable phenotypes include drug resistance markers, enzymes whose activity produces a detectable reaction product and the like. A preferred reporter gene is the beta-galactosidase gene (lacZ).

A preferred lacZ gene is one that utilizes alpha complementation, as described herein, whereby functional lacZ activity requires the association of the alpha portion of the lacZ gene product with the complementary portion of the lacZ referred to as the lacZ ▲ M15 gene product.

The test gene is operatively linked to prokaryotic expression signals to facilitate the rapid detection of mutations by the present invention. Upon excision rescue of a target gene system, the test gene system is introduced into a prokaryotic expression system, such as a bacterial cell lawn, so that dilutions of the test genes can be expressed and thereby observed (reported) to quantify the extent of test gene mutation.

Insofar as the expression of a test gene is measured in a prokaryotic expression system such as a bacterial cell, it is understood that the mutations can occur either in the structural portions of a test gene or in the expression control signals such as the prokaryotic promoter for expressing the test gene. Thus in preferred embodiments the test gene comprises a lacI or lacIq gene and includes a lacI promoter region.

A lambda phage of this invention comprises a target gene system that is excisably-integrated into the genome of an animal cell or embryo. By excisably-integrated is meant that the lambda phage comprises excision elements operatively linked to the genome that provide a means to conveniently remove the test gene system from the animal, cell or embryo genome subjected to mutagenesis conditions for the purpose of assessing the possible occurrence of mutation.

Exemplary excision elements are nucleotide sequences flanking the target gene, and if present the reporter gene, and other elements of the target gene system, that allow site-specific excision out of the genome to which the target gene system is operatively linked (integrated). Preferred nucleotide sequences are the cos sites, flp recombinase recognition sites, or loxP sites recognized by the Cre protein, all of whom are described more fully herein.

Preferred are cos site excision elements because of the convenience and the efficiency of excision of the genes contained between the two cos site nucleotide sequences when utilizing lambda bacteriophage in vitro packaging extracts as described herein.

The excision elements of a target gene system confer the ability to readily recover the target gene system from the mutagen exposure conditions to the prokaryotic expression medium in which the reporter gene is measured.

An exemplary and preferred test gene system is the lambda LIZ alpha vector described herein in which a lacIq test gene is operatively linked to the alpha-complementation-based lacZ alpha gene, where both test and reporter genes are under the control of prokaryotic expression signals, namely, lacI promoter and lacZ promoter/operator sequences.

This preferred system further contains nucleotide sequences operatively linked to the test gene that define a prokaryotic origin of replication, a selectable marker (amp$^R$) and a filamentous phage origin of replication such that the test gene can readily be transformed into a "f1-type" nucleic acid sequencing vector for rapid determination of the nature of the mutation in the test gene. This latter feature is provided according to the teachings of Short et al., *Nucl. Acids Res.*, 16:7583–7600 (1988), where the terminator and initiator domains of the f1 intergenic region are separated and flank the test gene sequences of this invention to be recovered and sequenced.

A promoter is a sequence of nucleotides that forms an element of a structural gene transcriptional unit which controls the gene's expression by providing a site for RNA polymerase binding resulting in the initiation of the process of transcription whereby a gene is transcribed to form a messenger ribonucleic acid (mRNA) molecule.

An operator is a sequence of nucleotides that forms a site for specific repressor binding. Thus, operators are specific for a particular repressor.

A repressor binding site is considered specific if the equilibrium binding constant for repressor binding to the operator is greater than $10^{-9}$ molar (M), preferably greater than $10^{-10}$M, and more preferably greater than $10^{-11}$M. The equilibrium binding constant for a repressor binding to an operator can readily be measured by well known equilibrium dialysis methods, or in a nitrocellulose filter binding assay where repressor is immobilized on nitrocellulose and $^{32}$P-labeled operator-containing DNA segment is presented in solution for binding to the immobilized repressor. See, Miller "Experiments in Molecular Genetics", p367–370, Cold Spring Harbor Laboratory, New York, 1972.

The operator for the lac repressor has been well characterized and is used as exemplary herein. See Miller et al , in "The Operon" Cold Spring Harbor Laboratory, New York (1980), for a detailed study. Alternative nucleotide sequences have been described for a lac repressor operator that specifically binds to repressor. See, for example, the description of numerous lac operator variants and the methods for characterizing their repressor-binding activity reported by Sartorius et al., *EMBO J.*, 8:1265–1270 (1989); and Sadler et al., *Proc. Natl. Acad. Sci. U.S.A.*, 80:6785–6789 (1983). Any nucleotide sequence that binds lac repressor specifically can be used in the present invention, although wild type and optimized operators are preferred and used as exemplary herein. The two optimized operators derived from the lac operon include the nucleotide sequences shown in SEQ. ID. NO. 1 and NO. 2 as follows:

(SEQ. ID NO. 1) 5'-TGT GGA ATT GTG AGC GCT CAC AAT TCC ACA-3'

(SEQ. ID NO. 2) 5'-ATT GTG AGC GCT CAC AAT-3'

Operators function to control the promoter for a structural gene by a variety of mechanisms. The operator can be positioned within a promoter such that the binding of the repressor covers the promoter's binding site for RNA polymerase, thereby precluding access of the RNA polymerase to the promoter binding site. Alternatively, the operator can be positioned downstream from the promoter binding site, thereby blocking the movement of RNA polymerase down through the transcriptional unit.

Multiple operators can be positioned on a rDNA molecule to bind more than one repressor. The advantage of multiple operators is several fold. First, tighter blockage of RNA polymerase binding or translocation down the gene can be effected. Second, when spaced apart by at least about 70 nucleotides and typically no more than about 1000 nucleotides, and preferably spaced by about 200 to 500 nucleotides, a loop can be formed in the nucleic acid by the interaction between a repressor protein bound to the two operator sites. The loop structure formed provides strong inhibition of RNA polymerase interaction with the promoter, if the promoter is present in the loop, and provides inhibition of translocation of RNA polymerase down the transcriptional unit if the loop is located downstream from the promoter.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art and include OriC as described herein. In addition, those embodiments that include a procaryotic replicon may also include a gene whose expression confers a selective advantage such as amino acid nutrient dependency or drug resistance to a bacterial host transformed therewith as is well known, in order to allow selection of transformed clones. Typical bacterial drug resistance genes are those that confer resistance to ampicillin as used herein, tetracycline, kanamycin, and the like.

Those vectors that include a procaryotic replicon may also include a procaryotic promoter capable of directing the expression (transcription and translation) of the gene transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Bacterial expression systems, and choice and use of vectors in those systems is described in detail in "Gene Expression Technology", *Meth. Enzymol.*, Vol 185, Goeddel, Ed., Academic Press, N.Y. (1990). Typical of such vector plasmids are pUC8, pUC9, pBR322 and pBR329 available from Bio-Rad Laboratories, (Richmond, Calif.) and pPL and pKK233-2, available from Pharmacia, (Piscataway, N.J.), or Clone Tech (Palo Alto, Calif.).

Transgenic Animals and Their Use

In one embodiment, the present invention provides novel transgenic non-human animals and methods for monitoring the mutagenic effects of potential mutagenic agents. In accordance with this invention, at least one copy of at least one target test DNA sequence is introduced into cells of a non-human mammal thereafter bred to produce test animals. Preferably, substantially all of the cells will contain the test DNA sequence. The test transgenic animal is then exposed to an agent suspected to be mutagenic and the test DNA sequence may be subsequently recovered from individual tissues of the transgenic animal. The test DNA sequence may be transferred into a microorganism, although such recovery and transfer is not requisite, and assayed for mutations, allowing rapid examination of multiple tissue specific genetic mutations. Other methods to monitor mutations in the test DNA need not rely on rescue and involve either direct examination of the test DNA in situ, PCR amplification of the test DNA, examination of RNA transcription products of the test DNA or protein translation products of said RNA, or effects of said proteins or substrates for said proteins.

Theoretically, any animal suitable for mutagenic testing may be used as the starting organism. In order to allow for ubiquitous insertion of the novel test sequence, single cell animal embryos are harvested, although there may be other cells facilitating the uptake and ultimate ubiquitous presence of the marker DNA in cells of a differentiated animal.

In accordance with the invention, any number or variety of sequences coding for a phenotype or genotype that is detectable upon mutation may be used for introduction into the transgenic non-human mammals of the invention. Vectors capable of facilitating the recovery of the test DNA sequence from the host mammal cells, and capable of allowing replication and expression of the sequence in a bacterial host, are preferably used as carriers for the target test DNA sequence. Accordingly, the construct for such a vector and insert preferably should contain regions for excision from the mammal host genome, and regions that allow replication in a bacterial host cell, as well as regions that permit expression and assay of the test DNA sequence. If integration into the host genome is not required, desired regions that allow for replication of the test DNA sequence in the animal host cells should be present. Elbrecht et al., Episomal Maintenance of a Bovine Papilloma Virus Vector in Transgenic Mice, *Mol. Cell. Biol.*, 7:1276–1279 (1987).

Further, in accordance with the invention, the test DNA sequence is introduced into the host mammal, preferably (but not necessarily) at the single-cell embryo stage, so as to provide the stable presence of the test sequence throughout cells of the differentiated animal. The use of chimeric animals is also contemplated herein. Typically, this involves the integration of the test DNA sequence into the mammal host genome, although methods that allow the test sequence to be stably and heritably present through the use of autonomously replicating vectors will also be useful. Elbrecht et al., Episomal Maintenance of a Bovine Papilloma Virus Vector in Transgenic Mice. *Mol. Cell. Biol.*, 7:1276–1279 (1987). At the cellular level, this may be accomplished using the techniques of microinjection, electroporation, dielectrophoresis or various chemically mediated transformation techniques, all of which are well known in the art. At the differentiated tissue level, other techniques may be necessary.

Following the introduction of the test DNA sequence and integration into the genome or cell, the transgenic cell or cells must be allowed to differentiate into a whole organism. This may be accomplished, for example, by embryo implantation into pseudopregnant females, or by other techniques allowing maturation of transgenic embryos. Once such maturation and differentiation has occurred, the animal is assayed for the presence of the test DNA sequence. Typically this involves removing small portions of tissue from the animal and using standard DNA hybridization assay techniques to detect the presence of the test DNA sequence.

Transgenic animals carrying the test DNA sequence are thereafter bred and offspring carrying the test DNA sequence my be selected for mutagenesis testing. In accordance with the invention, the selected transgenic mammals are exposed to agents or substances in question under appropriate conditions. Such conditions will depend, for example, on the nature of the agent or substance, the purpose of the mutagenesis study and the type of data desired.

After exposure of test transgenic animals to the agent to be tested under the desired conditions, desired tissue may be removed from the test animal. Because in the preferred embodiment the test DNA sequence is present in essentially all tissues, the tissue type tested is not limited by the process of insertion of the test DNA sequence. Any desired tissue may be removed and assayed at the DNA, RNA, protein or substrate/product level, by various methods including, but not limited to, in situ hybridization to the DNA or RNA, PCR, protein or enzymatic assays (*PCR Protocols, A Guide to Methods and Applications,* eds. Innis, M. et al., Academic Press, Inc., 1990; Maniatis et al., *Molecular Cloning. A Laboratory Manual,* Cold Spring Harbor, N.Y. 1982).

Alternatively, genomic DNA may be purified from the tissue. The target test DNA sequence which is integrated may then be rescued from the total genomic DNA of the host. This may be accomplished by excising it from the host genome or by suitable procedures allowing separation by size, weight or charge density. The method of rescue is dependent upon whether test DNA sequence is inserted into the genome, and whether flanking regions allow for excision, or whether the test DNA sequence is part of a replicating element allowing for separation techniques.

The rescued test DNA sequences may then be transferred into and expressed by microorganisms suitable for large scale screening techniques. In a preferred embodiment, this involves excising the test DNA sequence vector from the genomic DNA by packaging the test DNA sequence with bacteriophage packaging techniques. This may require ligating the test DNA sequence into an appropriate vector or merely involve direct transformation into a microorganism.

Microorganisms containing the test DNA sequence vector are thereafter grown on indicator plates or in selective media. Those organisms have a phenotype indicating mutation of the test DNA sequence are considered to contain a mutated test DNA sequence. The ratio of those organisms expressing mutated phenotype of test sequences to the total number of organisms containing the test DNA sequence is a measure of the mutagenicity of the agent and metabolites of it present in the tested tissue.

Bacteriophage packaging techniques involve the use of bacteriophage-infected host cell extracts to supply the mixture of proteins and precursors required for encapsidating the bacteriophage DNA from exogenous sources. We have recently discovered that the rescue efficiency of the test DNA sequence can be significantly increased by eliminating the restriction systems in the strain of host microorganism used both for preparing the packaging extracts as well as those microorganisms used for plating to detect mutagenesis. Additionally, other recovery systems, e.g., DNA transformation of isolated genomic DNA, would be improved by removal of such restriction systems or activities.

By removing these restriction systems which recognize and deactivate foreign DNA, rescue efficiencies may be increased up to at least 12,000 pfu/μg genomic DNA. These rescue efficiencies enable several million target genes from each tissue be analyzed, generating a large number of data points and resulting in a significant reduction in the numbers of animals required for mutagenesis testing with greater statistical significance.

Accordingly, the integrated target test DNA sequence is, preferably, rescued from the total genomic DNA of the host mammal using a lambda packaging extract deficient in restriction systems which recognize and deactivate foreign DNA. The rescued test DNA sequences may then be transferred into and expressed by restriction system deficient microorganisms.

Alternatively, a shuttle vector system can be constructed which provides rapid analysis of test DNA sequence. The test DNA sequence may be contained within a system which allows excision and recircularization of the test DNA sequence, which system is contained by a bacteriophage sequence. Following rescue of the bacteriophage genome containing test DNA sequence using packaging extracts, the test DNA may be further excised from the bacteriophage genome and recircularized to provide for rapid mutation analysis.

Further, the present invention contemplates the performance of mutagenesis testing by examining the phenotypes of cells containing the test DNA sequence without recovery of the test DNA sequence from the cell. This may be accomplished by the sectioning of tissues of the transgenic mammal of the invention, after exposure to a potential mutagenic agent, and assaying the genotype or phenotype of the test DNA sequence by in situ hybridization or, e.g., by staining of the tissue sections.

The present invention has application in the genetic transformation of multicellular eukaryotic organisms which undergo syngamy, i.e., sexual reproduction by union of gamate cells. Preferred organisms include non-human mammals, birds, fish, gymnosperms and angiosperms.

In one embodiment, the present invention contemplates a transgenic fish for the in vivo screening for mutagenic compounds. Fish represent a category of animals of great interest for agricultural and ecological reasons in the context of water-borne mutagenic compounds, and provide a convenient system for screening mutagenic compounds in a variety of fish species including, but not limited to, trout, salmon, carp, shark, ray, flounder, sole, tilapia, medaka, goldfish, guppy, molly, platyfish, swordtail, zebrafish, loach, catfish, and the like.

Transgenic fish of numerous species have been prepared, providing the skilled practitioner with a variety of procedures for developing a transgenic fish having an excisably-integrated target gene according to the present invention. See, for example, the teachings of Ozato et al, *Cell Differ.*, 19:237–244 (1986), Inoue et al, *Cell Differ. Dev.*, 29:123–128 (1990), Rokkones et al, *J. Comp. Physiol. B*, 158:751–758 (1989), and Guyomard et al, *Biochimie*, 71:857–863 (1989), that describe preparation of transgenic medaka, medaka, salmon and trout, respectively.

Thus, the present invention contemplates a non-human animal containing a modified lambda bacteriophage (rDNA) of the present invention excisably-integrated in the genome of the animal's somatic and germ cells, i.e., a transgenic animal. Particularly preferred are transgenic mammals, and are utilized as exemplary herein.

Mammals containing a rDNA of the present invention are typically prepared using the standard transgenic technology described in Hogan et al., *Manipulating the Mouse Embryo: A Laboratory Manual*, Cold Spring Harbor, N.Y. (1987); and Palmiter et al., *Ann. Rev. Genet.*, 20:465–499 (1986); which methods are described further herein. Production of transgenic mammals is also possible using the homologous recombination transgenic systems described by Capecchi, *Science*, 244:288–292 (1989). Preparation of transgenic mammals has also been described in U.S. Pat. No. 4,736, 866, No. 4,870,009, No. 4,873,191 and No. 4,873,316.

One technique for transgenically altering a mammal is to microinject a rDNA into the male pronucleus of the fertilized mammalian egg to cause one or more copies of the rDNA to be retained in the cells of the developing mammal. Usually up to 40 percent of the mammals developing from the injected eggs contain at least 1 copy of the rDNA in their tissues. These transgenic mammals usually transmit the gene through the germ line to the next generation. The progeny of the transgenically manipulated embryos may be tested for the presence of the construct by Southern blot analysis of a segment of tissue. Typically, a small part of the tail is used for this purpose. The stable integration of the rDNA into the genome of the transgenic embryos allows permanent transgenic mammal lines carrying the rDNA to be established.

Alternative methods for producing a non-human mammal containing a rDNA of the present invention include infection of fertilized eggs, embryo-derived stem cells, totipotent embryonal carcinoma (Ec) cells, or early cleavage embryos with viral expression vectors containing the rDNA. See for example, Palmiter et al., *Ann. Rev. Genet.*, 20:465–499 (1986) and Capecchi, *Science*, 244:1288–1292 (1989).

A transgenic mammal can be any species of mammal, including agriculturally significant species, such as sheep, cow, lamb, horse and the like. Preferred are animals significant for scientific purposes, including but not limited to rabbits, primates and rodents, such as mice, rats and the like. A transgenic mammal is not human.

Methods of Genetically Programming a Cell Within an Organism With A Target Gene System The present invention also contemplates a method of introducing a target gene system into a cell, i.e., genetically programming a cell within an organism by introducing a modified lambda genome containing a target gene system of the present invention into the genome of a zygote to produce a genetically altered zygote, or into the genome of individual somatic cells in the organism. The genetically altered zygote is then maintained under appropriate biological conditions for a time period equal to a gestation period or a substantial portion of a gestation period that is sufficient for the genetically altered zygote to develop into a transgenic organism containing at least 1 copy of the rDNA.

The term "genetically programming" as used herein means to permanently alter the DNA content of a cell within an organism such as a mammal so that a prokaryotic target gene system has been introduced into the genome of the cells of the organism.

Any multicellular eukaryotic organism which undergoes sexual reproduction by the union of gamete cells may be genetically programmed using an rDNA of the present invention. Examples of such multicellular eukaryotic organisms include amphibians, reptiles, birds, mammals, bony fishes, cartilaginous fishes, cyclostomes, arthropods, insects, mollusks, thallaphytes, embryophytes including gymnosperms and angiosperms. In preferred embodiments, the multicellular eukaryotic organism is a mammal, bird, fish, gymnosperm or an angiosperm.

A transgenic organism is an organism that has been transformed by the introduction of a recombinant nucleic acid molecule into its genome. Typically, the recombinant nucleic acid molecule will be present in all of the germ cells and somatic cells of the transgenic organism. Examples of transgenic organisms include transgenic mammals, transgenic fish, transgenic mice, transgenic rats and transgenic plants including monocots and dicots. See for example, Gasser et al., *Science*, 244:1293–1299 (1989); European Patent Application No. 0257472 filed Aug. 13, 1987 by De La Pena et al.; PCT Pub. No. WO 88/02405 filed Oct. 1, 1987 by Trulson et al.; PCT Pub. No. WO 87/00551 filed Jul. 16, 1986 by Verma, and PCT Pub. No. WO 88/09374 filed May 20, 1988 by Topfer et al.

Methods for producing transgenic organisms containing a rDNA of the present invention include standard transgenic technology; infection of the zygote or organism by viruses including retroviruses; infection of a tissue with viruses and then reintroducing the tissue into an animal; and introduction of a rDNA into an embryonic stem cell of a mammal followed by appropriate manipulation of the embryonic stem cell to produce a transgenic animal. See for example, Wagner, et al., U.S. Pat. No. 4,873,191 (Oct. 10, 1989); Rogers, et al., *Meth. in Enzymol.*, 153:253–277 (1987); Verma et al., PCT Publication No. W087/00551; Cocking et al., *Science*, 236:1259–1262 (1987); and Luskin et al., *Neuron* 1:635–647 (1988).

Transgenic mammals having at least 1 cell containing the rDNA's of a prokaryotic gene regulation system of the present invention can be produced using methods well known in the art. See for example, Wagner et al., U.S. Pat. No. 4,873,191 (Oct. 10, 1989); Hogan et al., Manipulating the Mouse Embryo: A Laboratory Manual, Cold Springs Harbor, New York (1987); Capecchi, *Science*, 244:288–292 (1989); and Luskin et al., *Neuron* 1:635–647 (1988).

In preferred embodiments the transgenic mammal of the present invention is produced by:

1) microinjecting a subject rDNA into a fertilized mammalian egg to produce a genetically altered mammalian egg;

2) implanting the genetically altered mammalian egg into a host female mammal;

3) maintaining the host female mammal for a time period equal to a substantial portion of a gestation period of said mammal;

4) harvesting a transgenic mammal having at least one cell containing a rDNA that has developed from the genetically altered mammalian egg.

A fertilized mammalian egg may be obtained from a suitable female mammal by inducing superovulation with gonadotropins. Typically, pregnant mare's serum is used to mimic the follicle-stimulating hormone (FSH) in combination with human chorionic gonadotropin (hCG) to mimic luteinizing hormone (LH). The efficient induction of superovulation in mice depends as is well known on several variables including the age and weight of the females, the dose and timing of the gonadotropin administration, and the particular strain of mice used. In addition, the number of superovulated eggs that become fertilized depends on the reproductive performance of the stud males. See, for example, *Manipulating the Embryo: A Laboratory Manual,* Hogan et al., eds., Cold Spring Harbor, N.Y. (1986).

The rDNA may be microinjected into the mammalian egg to produce a genetically altered mammalian egg using well known techniques. Typically, the rDNA is microinjected directly into the pronuclei of the fertilized mouse eggs as has been described by Gordon et al., *Proc. Natl. Acad. Sci., USA,* 77:7380–7384 (1980). This leads to the stable chromosomal integration of the rDNA in approximately 10 to 40 percent of the surviving embryos. See for example, Brinster et al., *Proc. Natl. Acad. Sci., U.S.A.,* 82:4438–4442 (1985). In most cases, the integration appears to occur at the 1 cell stage, as a result the rDNA is present in every cell of the transgenic animal, including all of the primordial germ cells. The number of copies of the foreign rDNA that are retained in each cell can range from 1 to several hundred and does not appear to depend on the number of rDNA injected into the egg as is well known.

An alternative method for introducing genes into the mouse germ line is the infection of embryos with virus vectors. The embryos can be infected by either wild-type or recombinant viruses leading to the stable of integration of viral genomes into the host chromosomes. See, for example, Jaenisch et al., *Cell,* 24:519–529 (1981). One particularly useful class of viral vectors are virus vector derived from retroviruses. Retroviral integration occurs through a precise mechanism, leading to the insertion of single copies of the virus on the host chromosome. The frequency of obtaining transgenic animals by retroviral infection of embryos can be as high as that obtained by microinjection of the rDNA and appears to depend greatly on the titre of virus used. See, for example, van der Putten et al., *Proc. Natl. Acad. Sci., USA,* 82:6148–6152 (1985).

Another method of transferring new genetic information into the mouse embryo involves the introduction of the rDNA into embryonic stem cells and then introducing the embryonic stem cells into the embryo. The embryonic stem cells can be derived from normal blastocysts and these cells have been shown to colonize the germ line regularly and the somatic tissues when introduced into the embryo. See, for example, Bradley et al., *Nature,* 309:255–256 (1984). Typically, the embryo-derived stem cells are transfected with the rDNA and the embryo-derived stem cells further cultured for a time period sufficient to allow the rDNA to integrate into the genome of the cell. In some situations this integration may occur by homologous recombination with a gene that is present in the genome of the embryo-derived stem cell. See, for example, Capecchi, *Science,* 244:1288–1292 (1989). The embryo stem cells that have incorporated the rDNA into their genome may be selected and used to produce a purified genetically altered embryo derived stem cell population. See, for example, Mansour et al., *Nature,* 336:348 (1988). The embryo derived stem cell is then injected into the blastocoel cavity of a preimplantation mouse embryo and the blastocyst is surgically transferred to the uterus of a foster mother where development is allowed to progress to term. The resulting animal is chimeric in that it is composed from cells derived of both the donor embryo derived stem cells and the host blastocyst. Heterozygous siblings are interbred to produce animals that are homozygous for the rDNA. See for example, Capecchi, *Science,* 244:1288–1292 (1989).

The genetically altered mammalian egg is implanted into host female mammals. Methods for implanting genetically altered mammalian eggs into host females are well known. See, for example, Hogan et al., *Manipulating the Mouse Embryo: A Laboratory Manual,* Cold Spring Harbor Laboratory, Cold Spring Harbor, N.Y. (1986). Pseudopregnant recipient females may be produced by mating females in natural estrus with vasectomized or genetically sterile males. After mating with a sterile male, the female reproduction tract becomes receptive for transferred embryos even though her own unfertilized eggs degenerate. The genetically altered mammalian eggs are then transferred to the ampullae or the uterine horns of the pseudopregnant recipient. If the genetically altered mammalian egg is transferred into the ampullae it must be enclosed in a zona pellucida membrane. If it is transferred into the uterine horns the genetically altered mammalian egg does not require a zona pellucida membrane.

The host female mammals containing the implanted genetically altered mammalian eggs are maintained for a sufficient time period to give birth to a transgenic mammal having at least 1 cell containing a rDNA of the present invention that has developed from the genetically altered mammalian egg. Typically this gestation period is between 19 to 20 days depending on the particular mouse strain. The breeding and care of mice is well known. See for example, *Manipulating the Mouse Embryo: A Laboratory Manual,* Hogan et al., eds., Cold Spring Harbor, N.Y., (1986).

The infection of cells within an animal using a replication incompetent retroviral vector has been described by Luskin et al., *Neuron,* 1:635–647 (1988).

In one embodiment, an animal that contains a target gene system in specific tissues or cells is used to test the effect of a material, composition, or compound suspected of being a carcinogen on the specific tissue. The animal is exposed to the particular material or compound and the mutagenic effect on the animal is determined by the derepression of the operator-regulated reporter gene segment as an indication of the carcinogenicity of the compound or material.

The composition suspected of having carcinogenic activity is introduced into the animal by any suitable method including injection, or ingestion or topical administration.

The animal is then maintained for a predetermined time period that is sufficient to allow the composition to produce a mutagenic effect on the genes of the target gene system. Typically, this time period ranges from several minutes to several days depending on the time the composition requires to mutagenize the genes.

The physiological process or parameter assayed as an indication of mutagenesis depends upon the particular physiological alteration produced by the expression of the reporter gene.

A change in a physiologic parameter is determined by measuring that parameter before introduction of the composition into the animal and comparing that measured value to a measured value determined in identical manner after introduction of the composition into the animal.

The copy number of the test gene in the transgenic animals alters the sensitivity of transgenic animals to the effects of the suspected carcinogen. Therefore, selection of transgenic animals with varying transgene copy numbers of the test gene will alter the sensitivity of the transgenic mice to the suspected carcinogen.

Prolysogenic Microorganisms

The present invention also contemplates a selectable system for screening (testing) for the presence of mutagenic activity upon the target gene system of this invention that utilizes a prolysogenic microorganism to provide positive selection for mutagenized target genes. Thus, the invention also contemplates a prolysogenic microorganism for use in the system and methods of this invention.

A prolysogenic microorganism (prolysogen) is a microorganism containing an isolated bacteriophage cI gene. By "isolated bacteriophage cI gene" is meant a cI gene separated from other bacteriophage genes. The isolated cI gene is present in the microorganism operatively linked to expression control elements for producing a bacteriophage lytic cycle-suppressing amount of cI gene product in the microorganism. The microorganism can be any microorganism, such as a yeast, bacterium and the like, adapted for infection by a bacteriophage, preferably a strain of E. coli.

A lytic cycle-suppressing amount of cI gene product is an amount sufficient to prevent a lambda bacteriophage-infected cell from lysing during the lytic phase of the bacteriophage's life cycle. The study of bacteriophage lambda is extensive in the biological arts, and the life cycle, and the lytic and lysogenic phases of the lambda life cycle are extremely well characterized. Thus assays for determining whether the cI amount is sufficient for suppression of the lytic cycle, and produce a lysogenic infection, is well known in the art.

The microorganism expressing a lytic cycle-suppressing amount of cI gene product is referred to as a prolysogen to connote its ability to impose a lysogenic life cycle upon a lambda-infected cell, even if the lambda would otherwise have the ability to be lytic. The control of lytic versus lysogenic life cycles for lambda bacteriophage is well known to reside in the expression of the cI gene product.

In preferred embodiments, the prolysogen is phage-free, i.e., is free of genetic material recoverable via a bacteriophage packaging extract.

Further preferred is a prolysogen that is restriction system deficient, e.g., a prolysogenic strain of E. coli deficient in one or more of the mcrA, mcrB, mrr, hsdR restriction systems and the like. It is preferred that the prolysogen not contain any restriction system similar to a restriction system found in the minute 98 region of E. coli K-12.

Methods for producing an isolated cI gene are well known in the art. A preferred method utilizes PCR amplification of the gene and its native promoter as a single DNA segment no more than about 1000 nucleotides in length. Typical and preferred are the methods described herein. When genomic integration is desired, the cI gene-containing DNA segment is then typically operatively linked to an genomic insertion element, such as a transposon, or the insertion elements of the transposon. Alternatively, the cI gene-containing DNA segment can be linked to a plasmid capable of low copy number maintenance in the host.

The amount of cI gene, and therefore the amount of cI gene product expressed can vary, so long as the amount is sufficient to suppress lytic cycle, as described previously. To that end, the number of copies of the cI gene can vary, although typically 1 to 4 copies are preferred, particularly 1 copy as demonstrated herein in the preferred embodiment of the SCS-8cI lysogen.

The preparation and use of the SCS-8cI lysogen in the screening/testing to quantitate the amount of mutageneized target gene in a selectable system is described in more detail in Example 8.

Also contemplated is a kit for practicing the methods of the present invention that comprise, in an aliquot, a prolysogen of this invention. A kit can further contain a lambda phage packaging extract of this invention for use with the prolysogen, and having a restriction system deficiency compatible with the prolysogen.

EXAMPLES

The following examples are intended to illustrate, but not limit, the present invention. Accordingly, variations and equivalents, now known or later developed, that would be within the purview of one skilled in this art are to be considered to fall within the scope of this invention, which is limited only as set forth by the appended claims.

1. Construction of E. coli RecA– Lysogen Strains

Strains BHB2688R⁻ and BHB2690R⁻ are constructed using recA+ transformants of E. coli strains BHB2688 and BHB2690, respectively, as the recipients and any E. coli K-12 strain that carries a Tn10 (tetracycline resistant) in (or near) the mcrA gene (relevant genotype=mcrA:Tn10(tet$^R$)) as the donor. BHB2688, which is E⁻, and BHB2690, which is D⁻, are available from the American Type Culture Collection (ATCC), Rockville, Md. under the accession numbers 35131 and 35132, respectively. RecA+ transformation is accomplished by standard methods, typically using a recA expressing plasmid. Step 1: A P1 lysate is made from the E. coli K-12 strain described above. Step 2: BHB2688 and BHB2690 are transduced with the P1 lysate (Miller, J., Experiments in Molecular Genetics, Cold Spring Harbor Lab., Cold Spring Harbor, N.Y. (1972)). Step 3: Tetracycline (tet$^R$) resistant colonies are selected and purified. Step 4: Loss of tetracycline resistance is selected for on Bochner plates (Bochner, B. R., et al., J. Bacteriol., 143:926–933 (1980)), and colonies are purified. Step 5: Lack of mcrA restriction activity is tested by comparing transformation efficiency of unmethylated pBR322 versus pBR322 that has been in vitro methylated by HpaII methylase (Raleigh, supra). A mcrA+ strain will show a greatly reduced efficiency with the methylated plasmid. If mcrA activity is absent, this strain is then called BHB2688mcrA⁻ and BHB2690mcrA⁻, To delete the mcrB locus in the above mcrA⁻ strains, a donor E. coli K-12 strain with the relevant genotypes mcrB::Tn10(tet$^R$), mrr::Tn5(kan$^R$) was used. Make a P1 lysate from an E. coli K-12 strain that carries a Tn10(tet$^R$) in the mcrB gene. The strain should also have a Tn5(kan$^R$) in the mrr gene. Step 7: Transduce the BHB2688 mcrA⁻ and BHB2690 mcrA⁻ recA+(tet$^S$) strain. Step 8: Select for tet$^R$ colonies. Purify one colony that is also kan$^R$. Step 9: Select for loss of tet$^R$ on Bochner plates (Bochner, supra). Step 10: Purify several colonies and test for sensitivity to tetracycline and kanamycin. Select colonies that are both tet$^S$ and kan$^S$. Step 11: Test for lack of mcrB restriction activity as done for the mcrA test, however in this case, the pBR322 should be in vitro methylated by AluI methylase (Raleigh, supra; Ross, supra). A mcrB+ strain will show a greatly reduced efficiency with the methylated plasmid. Test for mrr restriction activity by comparing plating efficiency of lambda versus lambda which has been in vivo methylated by Pst I methylase (Heitman, supra). An mrr+ strain will show reduced efficiency with the methylated lambda. Test for hsdR restriction activity by comparing plating efficiency of lambda versus lambda which has been in vito methylated by hsdM methylase (Wood, W., *J. Mol. Biol.,* 16:118–133, (1966); Adams, *Bacteriophages,* New York: Interscience 1959; Bickle, supra, at pp. 95–100). An hsdR+ strain will show reduced efficiency with unmethylated lambda. If a strain (purified colony) lacks all restriction activity mcrA, mcrB, mrr, hsdR and was constructed by this method, it should then contain a deletion throughout the mcrB region (▲mcrB). These strains are BHB2688R⁻ and BHB2690R⁻.

A. *E. coli* BHB2690R–

(1) Transduction to Obtain BHB2690mcrA– a) Preparation of a P1 Lysate

A bacteriophage P1 lysate, hereinafter referred to as P1, was made from any *E. coli* K12 strain that carries a tetracyline resistant Transposon 10 (Tn10) in or near the mcrA gene (Tn10::mcrA). Briefly, one drop from an overnight culture of K12 was admixed into 5 ml of LB broth (Luria-Bertani broth was prepared by admixing and dissolving 10 grams (g) bacto-tryptone, 5 g bacto-yeast extract and 10 g NaCl into 1 liter deionized water) containing $5 \times 10^{-3}$ molar (M) $CaCl_2$. The admixture was aerated by swirling until the cells were in exponential log phase growth and had reached a density of $2 \times 10^8$ cells/ml. P1 was preabsorbed by admixing $10^7$ phage to 1 ml of the above admixture followed by maintenance at 20 minutes in a 30 degrees Celsius (30° C.) waterbath to form a phage-cell admixture. LB-top agar, 2.5 ml, maintained at 45° C., was then admixed with the phage-cell admixture. The resultant agar-containing cell suspension was plated onto a freshly made LB plate which was maintained at 30° C. for 8 hours. At the end of the maintenance period, the soft agar layers was scraped into a small centrifuge tube. The scraped surface of the plate was then washed with 1 ml broth and the wash was collected for admixture with the scraped soft agar. Five drops of chloroform were added to the centrifuge tube followed by centrifugation to pellet cell debris. The resultant supernatant, containing the P1 lysate, was collected.

b) Transduction with P1 Lysates

In this invention, *E. coli* lysogen BHB2690 (ATCC # 35132) was used as the specific strain for transduction. *E. coli* BHB2690, which was RecA–, was first transformed with pJC859 to introduce a functional RecA protein into the lysogen. pJC859 was a plasmid in which the nucleotide sequence encoding RecA had been inserted at the Bam HI site of the plasmid *E. coli* vector, pBR322 (ATCC #31344). Maniatis et al., *Molecular Cloning: A Laboratory Manual,* Cold Spring Harbor Laboratory, 2nd ed., Sections 1.12 and 5.88, 1989; and U.S. Pat. No. 4,843,006 (in which the RecA promoter/operator and 150 amino acid residues of RecA coupled to a heterologous polypeptide sequence is described). For the transformation, *E. coli* BHB2690 competent cells were prepared following standard procedures familiar to one skilled in the art. Maniatis et al., supra, Section 1.76. Alternatively, competent cells can be obtained commercially.

Five ml of a fresh overnight culture of BHB2690 recA+ to be transduced was resuspended in 5 ml of buffer consisting of 0.1 M $MgSO_4$ and 0.5 mM $CaCl_2$ according to the procedure by Miller. Miller, *Experiments in Molecular Genetics.,* Cold Spring Harbor Laboratory, 1972. The BHB2690 recA+ cell suspension was then aerated by swirling at 30° C. for 15 minutes. To each of 5 small test tubes, 0.1 ml of the aerated suspended cells was added. One hundred microliters (ul) of P1 lysate, prepared above, was added to the first tube. The P1 lysate was serially diluted 10-fold for addition to the remaining tubes except for the last tube which did not receive P1 and, thus, served as a control. A tube without cells containing P1 was also used as an additional control. The P1 lysate was preabsorbed by maintaining the tubes at 30° C. in a water bath for 20 minutes. Two hundred ul of 1 M sodium citrate was then added to each of the prepared tubes and the contents of each tube was then plated on tetracycline-containing plates to select for tetracycline resistant ($tet^R$) colonies.

After maintaining the plates at 30° C. to allow for growth of colonies, $tet^R$ colonies were selected and purified following procedures well known to one skilled in the art. The $tet^R$ colonies were then replated on Bochner plates to select for the loss of tetR as described by Maloy. Maloy et al., *J. Bacteriol.,* 145:1110–1112 (1981). Briefly, tet-sensitive, $tet^S$, colonies were selected on a medium consisting of the following: 15 grams/liter (g/l) agar; 5 g/l tryptone broth; 5 g/l yeast extract; 4 milliliters/l (ml/l) chlortetracycline hydrochloride (12.5 milligram (mg)/ml); 10 g/l NaCl; 10 g/l $NaH_2PO_4H_2O$; 6 ml/l fusaric acid (2 mg/ml); and 5 g/l $ZnCl_2$ (20 millimolar (mM)). Chemicals were obtained from Sigma. (Sigma, St. Louis, Mo.).

Selected $tet^S$ colonies were then purified and tested for the lack of mcrA restriction activity. The determination of mcrA– strains was accomplished by comparing transformation efficiency of unmethylated pBR322 versus pBR322 that had been in vitro methylated by Hpa II methylase. A mcrA+ strain showed a greatly reduced efficiency with the methylated plasmid. BHB2690RecA+mcrA–; hereinafter designated BHB2690mcrA–, strains were, thus, determined and used to make BHB2690mcrB– transductions as described below.

(2) Transduction to Obtain BHB2690mcrB–

The BHB2690mcrA– strains prepared above were used in similar transductions to select for BHB2690mcrB– strains. For this procedure, a P1 lysate was prepared as described above from any *E. coli* K12 strain that carried a Tn10 ($tet^R$) in the mcrB gene (mcrB::Tn10 ($tet^R$)). The strain selected also carried the Tn5 with kanamycin (antibiotic) resistant gene ($kan^R$) in the mrr gene (mrr::Tn5 ($kan^R$)).

The *E. coli* BHB2690mcrA– ($tet^S$) strains were then transduced with P1 lysate [(mcrB::Tn10 ($tet^R$) and (mrr::Tn5 ($kan^R$)) as described in Example 1a above. $Tet^R$ colonies that were also $kan^R$ were selected and purified. The loss of $tet^R$ on Bochner plates was measured as described above. Colonies that were both $tet^S$ and $kan^S$ after selection on Bochner plates were purified.

The lack of mcrB restriction activity was performed as described for determining the lack of mcrA activity with the exception that pBR322 was in vitro methylated by Alu I methylase. A mcrB+ strain showed a greatly reduced efficiency with the methylated plasmid. The test for mrr restriction activity was accomplished by comparing plating efficiency of lambda versus in vivo methylated lambda (by Pst I methylase). A mrr+ strain showed reduced efficiency with the methylated lambda. A separate test for hsdR restriction activity was also performed as the lack of activity confirmed the deletion of the entire mcrB region. The hsdR restriction activity test was performed by comparing plating efficiencies of lambda versus lambda which had been in vivo methylated by hsdM methylase. A hsdR+ strain showed reduced efficiency with the unmethylated lambda. With these tests, a selected colony which lacks all restriction activity, mcrA, mcrB, mrr, and hsdR, and constructed using this transduction approach was shown to contain a deletion throughout the mcrB region. This strain was designated BHB2690R– and used in the preparation of extract for prehead as described in Example 2a.

B. *E. coli* BHB2688R–

*E. coli* BHB2688 strains containing RecA+ but lacking mcrA, mcrB, mrr and hsdR were prepared using the approach described above for preparing *E. coli* BHB2690R–. For the transductions, *E. coli* lysogen BHB2688 (ATCC # 35131) was used. The resultant strain, designated BHB2688R–, was used in the preparation of extract for protein donor a described in Example 2 below.

2. Preparation of Packaging Extracts from Two Lysogens

A. Preparation of Sonicated Extract from Induced *E.coli* Strain BHB2690R– Cells For preparing a sonicated extract of the *E. coli* lysogen, strain BHB2690R– (prehead donor) prepared in Example 1a, the genotype of the strain is first verified before large-scale culturing. The presence of the mutation that renders the bacteriophage cI gene product temperature-sensitive is determined by streaking from the master stocks of *E. coli* BHB2690L– onto two LB agar plates. One of the plates is maintained at 32° C. while the other is maintained at 45° C. Bacteria with intact cI only grow on the plates maintained at 32° C. A single small colony of *E. coli* BHB2690R– is picked and maintained overnight at 32° C. and 45° C. The bacteria with the mutation only grow at 32° C. and grow slowly due to the recA– mutation present in the BHB strains. A 100 ml subculture of the verified master stock of *E. coli* strain BHB2690R– is then prepared and maintained overnight at 32° C.

After maintaining the *E. coli* BHB2690R– culture overnight, the optical density (OD) is measured at a wavelength of 600 nm. An aliquot of the overnight culture is admixed into 500 ml of NZM broth (NZM broth is prepared by admixing 10 g NZ amine, 5 g NaCl, and 2 g $MgSO_4\text{-}7H_2O$ to 950 ml of deionized water; the pH of the solution containing dissolved solutes is adjusted to pH 7.0 with 5 N NaOH), prewarmed to 32° C., in a 2-liter flask, to result in a starting $OD_{600}$ of approximately 0.1. The bacterial admixture is then maintained at 32° C. with vigorous agitation (300 cycles/minute in a rotary shaker) until an $OD_{600}$ of approximately 0.3 is reached. The $OD_{600}$ of 0.3 is generally attained within 2 to three hours of maintaining the culture. The cultures must be in the mid-log phase of growth prior to induction as described below.

The lysogen is induced by placing the flask in a water bath preheated to 45° C. The flask is swirled continuously for 15 minutes. An alternative approach for inducing lysogen is to immerse the flask in a shaking water bath set at 65° C. The temperature of the fluid contents of the flask is monitored. When the fluid reaches 45° C., the flask is then transferred to a water bath set at 45° C. and maintained for 15 minutes. The induced cells are then maintained for 2 to 3 hours at 38° to 39° C. with vigorous agitation as described above. A successful induction is verified by the visual clearance of an added drop of chloroform to the culture.

Following the 2 to 3 hour maintenance period, the cells are recovered from the admixture by centrifugation at 4000 g for 10 minutes at 4° C. The resultant supernatant is decanted and any remaining liquid is removed with a pasteur pipette and a cotton swab. The walls of the centrifuge bottle are wiped dry with towels. To the pelleted induced bacterial cells, 3.6 ml of freshly prepared sonication buffer is admixed. Sonication buffer consists of 20 mM Tris-HCl, pH 8.0, (Tris[hydroxymethyl]-aminomethane hydrochloride), 1 mM EDTA, pH 8.0, (ethylenediaminetetraacetic acid) and 5 mM beta-mercaptoethanol. The bacterial cell pellet is resuspended in the sonication buffer by mixing to form a homogenized cell suspension.

The resultant suspension is transferred to a small, clear plastic tube (Falcon 2054 or 2057, Falcon, Oxnard, Calif.) for subsequent sonication. The cells are disrupted by sonication with 10 second bursts at maximum power using a microtip probe. For sonication, the tube containing the suspension is immersed in ice water and the temperature of the sonication buffer should not be allowed to exceed 4° C. The sample is cooled for 30 seconds in between each sonication burst. The sonication procedure is continued until the solution in the tube clears and its viscosity decreases. The sonicated bacterial sample is transferred to a centrifuge tube and debris is pelleted by centrifugation at 12,000 g for 10 minutes at 4° C. forming a clear supernatant.

The resultant supernatant containing preheads is removed and admixed with an equal volume of cold sonication buffer and one-sixth volume of freshly prepared packaging buffer to form a diluted prehead admixture. Packaging buffer consists of the following: 6 mM Tris-HCl, pH 8.0; 50 mM spermidine; 50 mM putrescine; 20 mM $MgCl_2$; 30 mM ATP, pH 7.0; and 30 mM beta-mercaptoethanol. The admixture is then dispensed into pre-cooled to 4° C. 1.5-ml microfuge tube in 15 ul aliquots. The caps of the microfuge tubes are then closed and the tubes are immersed briefly in liquid nitrogen for freezing. The frozen preheads in packaging buffer are then stored at –70° C. for long-term storage.

B. Preparation of Frozen-Thawed Lysate of Induced *E. coli* BHB2688R– Cells

A subculture of *E. coli* BHB2688R–, prepared in Example 1b above, for obtaining an extract of packaging protein donor is verified for the genotype and is prepared as described above for preparing *E. coli* BHB2690R–. Overnight cultures are maintained and lysogen is induced also as described above.

The induced *E. coli* BHB2688R– cells are pelleted by centrifugation at 4000 g for 10 minutes at 4° C. The resultant supernatant is removed and any excess liquid is removed. The pelleted cells are resuspended in a total of 3 ml of ice-cold sucrose solution (10% sucrose in 50 mM Tris-HCl, pH 8.0) to form a cell suspension. The resultant cell suspension is dispensed in 0.5 ml aliquots into each of six precooled to 4° C. microfuge tubes. Twenty-five ul of fresh, ice-cold lysozyme solution (2 mg/ml lysozyme in 10 mM Tris-HCl, pH 8.0) is admixed to each tube containing the cell suspension. The cell-lysozyme admixture is gently mixed to form an *E. coli* extract and then immersed in liquid nitrogen for freezing.

The frozen tubes are removed from the liquid nitrogen and the extracts are thawed on ice. Twenty-five ul of packaging buffer, as prepared above, is admixed to each tube containing thawed extract to form a packaging buffer-extract admixture. The separately prepared admixtures are then combined in a centrifuge tube and centrifuged at 45,000 g for 1 hour at 4° C. to form an supernatant containing packaging protein donor.

The resultant supernatant is removed and dispensed in 10 ul aliquots into precooled at 4° C. microfuge tubes. The caps of the tubes are closed and the tubes are then immersed in liquid nitrogen. The tubes are then removed from the liquid nitrogen and stored at –70° C. for long term storage.

3. In Vitro Packaging Using Two Extracts

The frozen tubes containing prehead and packaging donor extracts prepared in Example 2a and 2b, respectively, are removed from storage at –70° C. and allowed to thaw on ice. The frozen-thawed lysate containing the protein donor thaws first and is admixed to the still-frozen sonicated prehead extract to form a prehead-protein donor admixture. The resultant admixture is mixed gently until almost totally thawed. The DNA to be packaged (up to 1 ug dissolved in 5 ul of 10 mM Tris-HCl, pH 8.0, 10 mM $MgCl_2$) is admixed with the thawed combined extracts and mixed with a fine glass stirring rod to form a DNA-extract admixture. The admixture is then maintained for 1 hour at room temperature. To the admixture, 0.5 to 1 ml of SM (SM buffer is prepared by admixing 5.8 g NaCl, 2 g $MgSO_4$-$7H_2O$, 50 ml Tris-HCl, pH 7.5, and 5 ml 2% gelatin (w/v) to 1 liter of deionized water and adjusting the pH to 7.5) and a drop of chloroform is added and gently mixed. Debris is removed by centrifugation at 12,000 g for 30 seconds at room temperature in a microfuge. The resultant supernatant is removed and contains packaged bacteriophage DNA particles.

The titer of the viable bacteriophage particles is measured by plating on the appropriate indicator strains. Recombinant DNAs that are 90% or 80% of wild-type bacteriophage lambda in length are packaged with efficiencies that are 20-fold to 50-fold lower, respectively, than those obtained with unit-length bacteriophage lambda. The same packaging extracts may be used for the packaging of both bacteriophage lambda and cosmids.

4. Preparation of Transgenic Mice and Their Use

The following studies provide details of the manner in which the present invention may be made and used in order to achieve the rapid recovery and examination of test DNA sequences from transgenic animals.

A. DNA Test Sequence

The test sequence DNA can, theoretically, contain any number or variety of genes or other identifiable test DNA sequences. In the prototype described herein, an *E. coli* bacteriophage lambda genome has been engineered to carry lacZ, a beta-galactosidase test DNA sequence. Lambda shuttle vectors L2B (46.5 kb) or C2B (48.0 kb) may be used. The genotype of the modified lambda genome L2B is Lac5 delta (shind III lambda 2°–3°) srI lambda 3°–5°cI857 sXhL lambda 1° sScII lambda 4°. Before injecting it into mouse embryos as described below, this lambda DNA was diluted to a concentration of 10 micrograms per milliliter and the cos ends were annealed and ligated under conditions predominantly forming circular lambda phage monomers. Maniatis et al., *Molecular Cloning, A Laboratory Manual,* pp. 109–110, 383–389 (Cold Spring Harbor, N.Y. 1982).

In addition, a variation of L2B may be constructed that contains a plasmid sequence that can be readily excised from the lambda phage and contains the lacI repressor gene. This variation has several advantages. First, as discussed below, physical identification of phage carrying mutations will be facilitated since they will grow as blue plaques on a white background in the presence of X-gal (5-bromo-4-chloro-3-indolyl-β-D-galactopyranoside) without IPTG (isopropylβ-D-thiogalacto-pyranoside). This advantage will also simplify and reduce the cost of the assay since it will permit an increase in the density of phage per plate. Additionally, the lacI genetic systems of *E. coli* are the first systems that conveniently permitted the study of large numbers of mutations within procaryotes at the DNA level (Miller et al., *J. Mol. Biol.,* 109:275–302 (1977), Coulondre and Miller, *J. Mol. Biol.,* 117:275–302 (1977), Schaaper, *J. Mol. Biol.,* 189:273–284, (1986)), and the use of lacI will provide a test gene with significant historical mutational data for comparison between mutagenesis assays.

B. Creation of a Transgenic Animal

Mice were used as the test animal. (Hogan et al., *Manipulating the Mouse Embryo: A Laboratory Manual,* Cold Spring Harbor Laboratory, 1986). Single cell mouse embryos were harvested from female mice that were impregnated the evening before. The embryos were treated with hyaluronidase and briefly cultured in M16 medium.

The embryos were transferred to M2 medium on a microscope glass depression slide. The embryos were observed with a 40× objective and a 10× eyepiece using a Nikon Diaphot microscope equipped with Hoffman optics. The embryos were held in place with a holding pipet that had been rounded with a microforge. The positions of both the holding pipets and the injection pipets were controlled with micromanipulators. DNA as described above was loaded in the injection pipet at a concentration of 1 to 10 micrograms per milliliter. Approximately one picoliter, as judged by a refractile change (Hogan et al., supra) of the pronucleus, of DNA solution was injected into the male pronucleus.

After DNA injection, four hundred embryos were transferred to M16 medium and incubated at 37° C. in a 5% $CO_2$ atmosphere for one to two hours. One hundred fifty embryos survived microinjection. Lysed embryos were discarded and 30 embryos that appeared normal were transferred to one of the fallopian tubes of each of 5 pseudopregnant foster mothers. The transfers were performed under a dissecting microscope using general anesthesia (avertin).

Seven pups were born. After birth, newborn mice were kept with their foster mothers for 2 weeks, at which point they were then weaned and screened for DNA integration. A 2 cm portion of the tail was removed and homogenized in 2 ml of a solution of 0.1 M NaCl, 50 mM Tris-HCl, pH 7.5, 1 mM EDTA for short duration, but long enough to disrupt cell and nuclear membranes. The homogenized tissue was treated with 50 U/ml RNaseA and 0.1% SDS for 15 minutes at 37° C. The mixture was exposed to Proteinase K digestion for 3 hours at 55° C. followed by three extractions with phenol/chloroform. DNA was then precipitated by the addition of ethanol. After resuspending the precipitated DNA in 10 mM Tris pH 8.0, 0.5 mM EDTA, some of it was digested with BamHI endonuclease and electrophoresed through an 0.8% agarose gel. The DNA was denatured by soaking the gel in 1.5 M NaCl, 0.5 M NaOH for one hour and then neutralizing the DNA by soaking it in 1.5 M NaCl, 0.5 M Tris, pH 7.4 for 30 minutes. The gel was then soaked in 10× SSC for one hour. The DNA was then transferred from the gel into a nitrocellulose filter by the method of Southern, as described in Maniatis, supra.

The filter with transferred DNA was hybridized overnight with $^{32}P$ labeled lambda DNA prepared according to standard procedures by the method of nick translation. Maniatis, supra. Following this overnight hybridization, the filter was washed in 0.1 x SSC, 0.1% SDS at 50° C. and Kodak XAR film was exposed to it in order to identify lambda DNA present within the mouse genome. Lambda DNA, used as standards, that had been electrophoresed alongside the mouse genomic DNA were compared in intensity to the transgenic mouse DNA hybridized to the $^{32}P$ labeled lambda DNA to estimate the number of copies of test DNA per mouse cell. Three transgenic animals have been produced and identified by this technique.

Newborn mice tested for the presence of the test DNA sequence by the tail-blotting procedure (Hogan et al., *Manipulating the Mouse Embryo: A Laboratory Manual,* pp. 174–183, Cold Spring Harbor Laboratory, 1986) were found to carry the test DNA sequence in DNA isolated from their tails. Eight weeks after birth these transgenic mice were mated and their progeny were examined for the test DNA sequence. Approximately 50% of the resulting offspring carried the test DNA sequence, demonstrating that the original transgenic mice carried the test DNA sequence in their germ line and that this sequence was inherited normally. While transgenic lines having approximately one copy of the test DNA sequence per cell can be obtained, it will be understood by one skilled in the art that multiple copy numbers per cell are obtainable and may be useful for many different applications.

C. Mutagen Treatments

Six to eight week old transgenic male mice were treated on day 1 and day 4 by intraperitoneal injection of either 125 or 250 mg N-ethyl-N-nitrosourea (EtNu), per kg body weight. Control animals were injected with 100 mM phosphate buffer at 10 ml/kg body weight. Tissues were collected two hours after final injection.

D. Recovery of the Test DNA Sequence and Mutagenesis Testing

1. Recovery

In the embodiment described here, rescue of the marker DNA sequence was accomplished by containing it within a lambda bacteriophage genome. The entire lambda bacteriophage genome is excised from the mouse chromosome by the in vitro packaging extract. The packaging extract recognizes the cos sites of the integrated lambda DNA and packages the sequences between the cos sites into lambda phage particles, as shown in FIG. 1.

The test DNA sequence may be found within the genomic DNA purified from any tissue of the transgenic mouse. Since the test DNA sequence is contained within a lambda phage genome, it can be excised away from the remainder of genomic DNA by using a lambda phage packaging extract. Packaged lambda phage such as L2B or C2B, may then be plated on $E.\ coli$ cells for further evaluation.

Bacteriophage lambda DNA can be packaged in vitro using protein extracts prepared from bacteria infected with lambda phage lacking one or more genes for producing the proteins required for assembly of infectious phage particles. Typical in vitro packaging reactions are routinely capable of achieving efficiencies of $10^8$ plaque from units (pfu) per µg of intact bacteriophage lambda DNA. About 0.05–0.5 percent of the DNA molecules present in the reaction can be package into infectious virions.

Various genetic mutations affect different stages of bacteriophage lambda DNA packaging. For instance, the E protein is the major component of the bacteriophage head and is required for the assembly of the earliest identifiable precursor. Bacteriophages mutant in the E gene ($E^-$) accumulate all of the components of the viral capsid. The D protein is localized on the outside of the bacteriophage head and is involved in the coupled process of insertion of bacteriophage lambda DNA into the "prehead" precursor and the subsequent maturation of the head. Bacteriophages mutant in the D gene ($D^-$) accumulate the immature prehead but do not allow insertion of bacteriophage lambda DNA into the head. The A protein is involved in the insertion of bacteriophage lambda DNA into the bacteriophage prehead and cleavage of the concatenated precursor DNA at the cos sites. Bacteriophages mutant in the A gene ($A^-$) also accumulate empty preheads. Complementing extracts have been prepared from cells infected with $A^-$ and $E^-$ or $D^-$ and $E^-$ strains; alternatively, extracts prepared from cells infected with $A^-$ mutants can be complemented by the addition of purified wild-type A protein.

A bacteriophage lambda DNA packaging extract is a proteinaceous composition that is capable of packaging bacteriophage lambda DNA into infectious virus particles. Preferably, the lambda DNA packaging extracts useful in this invention have a packaging efficiency of at least $10^8$, and more preferably at least $10^9$, pfu/µg of intact lambda DNA.

The packaging extracts of this invention are usually prepared from cells containing bacteriophage lambda lysogens of the appropriate genotype, e.g., amber mutations in genes A, D, E and the like. In addition to lacking a functional lacZ gene, useful lysogens preferably have one or more of the following mutations:

cIts857 - specifies a temperature-sensitive bacteriophage lambda repressor molecule. This mutation causes lambda DNA to be maintained in the lysogenic state when the host bacteria are grown at 32° C.; bacteriophage growth is induced by transiently raising the temperature to 42°–45° C. to inactivate the repressor specified by the cI gene.

Sam7 - an amber mutation in the bacteriophage S gene that is required for cell lysis. This mutation causes capsid components to accumulate within SuIII$^-$ bacterial cells for 2–3 hours following induction of the cIts857 lysogen.

b-region deletion (b2 or b1007) - a deletion in the bacteriophage genome that effectively removes the lambda DNA attachment site (att). This mutation reduces, but does not entirely eliminate, the packaging of endogenous lambda DNA molecules in extracts made from the induced cells.

red3 (in lambda) and recA (in $E.\ coli$) - mutations that inactivate the generalized recombination systems of bacteriophage lambda and the host, thereby minimizing recombination between the endogenous lambda DNA in the extract and the exogenously added recombinant genomes.

Thus, in preferred embodiments, a lambda lysogen useful for producing a packaging extract is one deficient in one or more of the mcrA, mcrB, hsd and mrr restriction systems. The genes comprising these systems can be removed or inactivated by well known methods, such as by transduction, transposon (Tn) mutagenesis, and the like.

Packaging extracts are usually prepared from a lysogenic bacteria having one or more of the following mutations: mcrA$^-$, mcrB$^-$, mrr$^-$, hsdR$^-$, and preferably from K-12 ▲mcrB, BHB2690R$^-$, or BHB2668R$^-$, by growing the appropriate lysogenic bacteria to mid-log phase at 32° C., inducing lytic functions by inactivating the cI repressor protein by raising the temperature to 45° C. for 15 minutes, and then growing the cultures for an additional 2–3 hours at 38°–39° C. to allow packaging components to accumulate. Cell extracts are then prepared as described further herein.

2. Testing for Mutagenesis

For plating bacteria, β-galactosidase deficient $E.\ coli$, are grown in 1X TB (5 g/L NaCL, 10 g/L tryptone) supplemented with 0.2% maltose and 10 mM MgSO$_4$ overnight at 30° C. Cells are harvested by centrifugation and resuspended in 10 mM MgSO$_4$ in preparation for plating (Maniatis, supra).

In a typical experiment, 1–5 µg of genomic DNA are exposed to in vitro lambda phage packaging extract and incubated for 2 hours at room temperature. The packaging reaction is then diluted in 500 µl SM buffer (100 mM NaCL, 8 mM MgSO$_4$, 50 mM Tris, pH 7.5, and 0.01% gelatin) and incubated with the above described bacteria (2.0 mL of OD$_{600}$ = 0.5), and then plated onto NZY/agar Nunc Bioassay Dishes (245 mm×245 mm×20 mm) with molten top agar containing 1.25 mg/mL X-gal and 2.5 mM IPTG at a density of less than 20,000 pfu per plate. The plates are incubated overnight at 37° C.

For the lambda genomes containing the β-gal (not the lacI) gene, in the presence of X-gal and IPTG, the phage plaques turn blue if the beta-galactosidase sequence within the lambda genome has not mutated. However, a white plaque or faint blue plaque on the petri dish is evidence that a mutation in the beta-galactosidase sequence has, for example, altered the reading frame, altered essential codons, or has created stop codons in the sequence. These white or faint blue plaques will be scored as positive for mutations and they can be plaque purified and saved for further analysis. The ratio of white or faint blue to blue plaques minus background (mutation rate from non-mutagenesis potency of the agent being tested when compared with DNA extracted from mice that have not been treated with potentially mutagenic agents.

E. Methods for Increasing Efficiency of Test DNA Sequence Rescue

1. Demethylation

It is anticipated that test DNA sequence rescue efficiency can be influenced by the state of CpG methylation in the mouse chromosome. Highly methylated DNA may not be efficiently excised by lambda packaging extract, presumably because of inhibition of cleavage at the cos sites, inhibition of expression of lambda genes encoded on lambda phage, or restriction by E. coli restriction systems. This may be alleviated by placing transcriptional enhancers, promoters and/or other regions of the DNA which inhibit methylation near critical sites such as the cos site to reduce CpG methylation. The drug 5'-azacytidine can also be used to reduce the level of DNA methylation in the target cells prior to DNA purification and rescue. Jaenisch, R., et al., Proc. Natl. Acad. Sci. USA, 82:1451–1455 (1985). In such a procedure, fibroblast cell lines are obtained from organisms containing the test DNA sequence of interest. Adams, R. L. P., Cell Culture for Biochemists, pages 68–83 (1980) Elsevier/North Hollan Biomedical Press). The cells are exposed in vitro at 37° C., within 50 µM 5'azacytidine supplementing the culture medium. Upon DNA replication, the daughter DNA loses its CpG methylation, which eliminates the methylation of sites in the target vector, where the target vector is a lambda phage. The DNA from these fibroblasts is then exposed to in vitro packaging extract, as previously described.

Alternatively, organisms containing the test DNA sequence can be directly injected with a 1 mg/ml solution of 5'-azacytidine in 0.15 M NaCl. This is done over a period of at least about 4 days, with a total of 400 µg administered. Jaenisch, supra. After this treatment, DNA can be extracted from various tissues and packaged as before.

2. Removal of Packaging Extract and Plating Strain Restriction Systems

We have determined that the efficiency of test DNA sequence recovery is dependent on the genotype of both the bacterial strain used to generate the packaging extract as well as the plating strains used for mutagenesis testing. This is due to host-controlled restriction systems that enable a bacterial cell to identify and inactivate foreign DNA by endonuclease cleavage. DNA is susceptible to restriction by the endonucleic activity of the host unless it is protected by modifications, such as methylation of specific nucleotides. While methylation of specific nucleotides usually serves to protect DNA from restriction by the endonucleolytic activity of the host, methylation at some DNA sequences actually confers sensitivity to restriction. One example, the mcrB restriction system of E. coli K-12, is responsible for the biological inactivation of foreign DNA that contains 5-methylcytosine residues. Ross et al., Journal of Bacteriology, 171:1974–1981 (1989).

There are a number of restriction/methylation systems endogenous to E. coli which are capable of inactivating foreign DNa by endonuclease cleavage. The most widely known systems are hsd (Bickle, T. Nucleases, p. 85, Cold Spring Harbor Lab., Cold Spring Harbor, N.Y. 1982), mrr (Heirman, J. et al., J. Bacteriol., 169:3243–3250 (1987)), mcrA (Raleigh et al., PNAS, 83:9070–9074 (1986)) and mcrB (Raleigh, supra.). The hsd system works by selectively restricting DNA that is not protected by adenine methylation at the N-6 position in the sequence, $A^{6me}$ACNNNNNNGTGC [SEQ ID NO: 4] or $GC^{6me}$-ACNNNNNNGTT [SEQ ID NO: 5]. The mrr system also involves adenine methylation, however, in this case the methylation does not serve to protect the DNA, but serves to make the DNA vulnerable to the restriction system. The systems mcrA and mcrB are similar to mrr in that they recognize and restrict methylated DNA. However, these two systems differ from mrr in that they recognize methylated cytosine. Further, the mcrB function is provided by the products of at least two genes, mcrB and mcrC (Ross et al., J. Bacteriol., 171:1974–1981 (1989)). The recognition sequences for mcr and mrr are contemplated in the literature, but precise sequences are as yet unknown.

We found that efficiency of recovery of the lacZ construct from the transgenic animal genome was increased without the use of 5-azacytidine, by using lambda packaging extracts and E. coli plating strains lacking restriction systems that cleave eukaryotic DNA. By removing these restriction systems, rescue efficiencies have been increased up to at least 12,000 pfu/µg genomic DNA. Of course, one skilled in the art will recognize that "removal" of these restriction systems may be effected by deleting or inhibiting the activity of these restriction systems, and the term "restriction system deficient" includes, but is not limited to, removal of the restriction systems by either method. In addition, naturally occurring strains of E. coli that are deficient in these restriction systems may be isolated and used.

Identification of the genes responsible for the E. coli restriction systems was achieved by examination of the inhibitory effect of certain E. coli strains on the ability to recover lambda phage. Isolation of the responsible genes was achieved through the use of interrupted matings and P1 transduction. An approximately 200 kb region of DNA in E. coli K-12 was found to produce an inhibitory effect on the plating efficiency of the rescued vector. Further, the region responsible for decreasing rescue efficiency was found to be near 98 minutes in the E. coli K-12 genetic map (Bachmann, B. E. coli and S. Typhimurium: Cellular and MOlecular Biology, eds. Neidhart et al., ASM, WA, DC, 1987) in the approximately 2.6 kb mcrB region containing mcrB and mcrC.

The comparison of the rescue efficiency using E. coli strains with different restriction genotypes is shown in Table 1. The bacterial strains listed in Table 1 are available from the following source or reference: ED8767 (Ishiura, M. et al., Anal. Biochem., 176:117–127 (1988); ER1451 (New England BioLabs, Beverly, Mass.); LCK8 (B. Bachman, Yale E. coli Center); NM621 (N. Murray, Univ. of Edinburgh); K802, LE392, NM554, PLK-A, PLK-17, Y1088, E. coli C, Sure (Stratagene, La Jolla, Calif.)).

TABLE 1

| Strain | Restriction Genotype | | | | Plating Efficiency |
|--------|------|------|------|-----|------|
|        | hsdR | mcrA | mcrB | mrr |      |
| ED8767 | −    | −    | −    | +   | −    |
| ER1451 | −    | −    | −    | +   | −    |
| K802   | −    | −    | −    | +   | −    |
| LCK8   | −    | −    | −    | +   | −    |
| LE392  | −    | −    | +    | +   | −    |

TABLE 1-continued

| Strain | Restriction Genotype | | | | Plating Efficiency |
|---|---|---|---|---|---|
| | hsdR | mcrA | mcrB | mrr | |
| NM554 | − | − | − | + | − |
| NM621 | − | − | − | + | − |
| PLK-A | − | − | − | + | − |
| PLK-17 | − | − | − | + | − |
| Y1088 | − | − | + | (+) | − |
| E. coli C | − | − | − | − | + |
| RR1-A | − | − | − | − | + |
| K-12 ▲mcrB | ▲ | − | ▲ | ▲ | + |
| Sure™ | ▲ | − | ▲ | ▲ | + |

Strain RR1-A and K-12 ▲mcrB are constructed as described below.

Strain RR1-A is constructed with strain RR1 (Maniatis, supra) (relevant genotype= mcrA+, (tet$^S$)) as the recipient and any E. coli K-12 strain that carries a Tn10 (tetracycline resistant) in (or near) the mcrA gene (relevant genotype= mcrA::Tn10(tet$^R$)) as the donor. Step 1: A P1 lysate is made from the E. coli K-12 strain described above. Step 2: RR1 is transduced (Miller, J., *Experiments in Molecular Genetics*, Cold Spring Harbor Lab., Cold Spring Harbor, N.Y. (1972)). Step 3: Tetracycline resistant colonies are selected and purified. Step 4: Loss of tetracycline resistance is selected for on Bochner plates (Bochner, B. R., et al., *J. Bacteriol.*, 143:926–933 (1980)), and colonies are purified. Step 5: Lack of mcrA restriction activity is tested by comparing transformation efficiency of unmethylated pBR322 versus pBR322 that has been in vitro methylated by HpaII methylase (Raleigh, supra). A mcrA+ strain will show a greatly reduced efficiency with the methylated plasmid. If mcrA activity is absent, this strain is then called RR1-A.

Strain K-12▲mcrB is constructed using two donor E. coli K-12 strains with the relevant genotypes mcrB::Tn10(tet$^R$), mrr::Tn5(Kan$^R$) and mcrA::Tn10(tet$^R$) and a recipient E. coli K-12 with the relevant genotype recA+, tet$^S$. Steps 1–5: Perform steps 1–5 as described for construction of RR1-A. In step 2, transduce any E. coli K-12 recA+ strain. Step 6: Make a P1 lysate from an E. coli K-12 strain that carries a Tn10(tet$^R$) in the mcrB gene. Transduce the K-12 recA+ (tet$^S$) strain. Step 8: Select the tet$^R$ colonies. Purify one colony that is also kan$^R$. Step 9: Select for loss of tet$^R$ on Bochner plates (Bochner, supra). Step 10: Purify several colonies and test for sensitivity to tetracycline and kanamycin. Select colonies that are both tet$^S$ and kan$^S$. Step 11: Test for lack of mcrB restriction activity as done for the mcrA tet, however in this case, the pBR322 should be in vitro methylated by AluI methylase (Raleigh, supra; Ross, supra). A mcrB+ strain will show a greatly reduced efficiency with the methylated plasmid. Test for mrr restriction activity by comparing plating efficiency of lambda versus lambda which has been in vivo methylated by Pst I methylase (Heitman, supra). An mrr+ strain will show reduced efficiency with the methylated lambda. Test for hsdR restriction activity by comparing plating efficiency of lambda versus lambda which has been in vitro methylated by hsd Mmethylase (Wood, W., *J. Mol. Biol.*, 16:118–133 (1966); Adams, *Bacteriophages*, New York: Interscience 1959; Bickle, supra, at pp. 95–100). An hsdR+ strain will show reduced efficiency with unmethylated lambda. If a strain (purified colony) lacks all restriction activities, namely, mcrA, mcrB, mrr, hsdR and was constructed by this method, it should then contain a deletion throughout the mcrB region (▲mcrB). It will then also very efficiently plate lambda that has been rescued from the mouse. This strain is called K-12 ▲mcrB.

The "▲" symbol in Table 1 indicates that the strain contains a large deletion in the mcrB region. All other mcrB− strains listed in Table 1 are K-12 derivatives believed to contain a small mutation in the mcrB region, with the exception of E. coli C which does not contain the K-12 mcrB region, and RR1-A which carries the wild type mcrB locus of E. coli B. It is known that all of these strains plate control L2B phage (amplified in hsdM+ E. coli K-12 rather than rescued from the mouse) with equal efficiency (within 1–4 fold). Rescued L2B phase were recovered from the mouse genome using mcr− E. coli K-12 lambda packaging extracts (Gigapack II - Stratagene, La Jolla, Calif.) and plated onto the indicated bacterial strains. A "+" plating efficiency of phage indicates that approximately 500 pfu/0.05 µg of transgenic mouse genome DNA was observed, while a "−" plating efficiency indicates that less than 5 pfu/0.05 µg of transgenic mouse genome DNA was observed. Note also that (+) indicates that the mrr activity has not been confirmed in Y1088.

Figure 3:
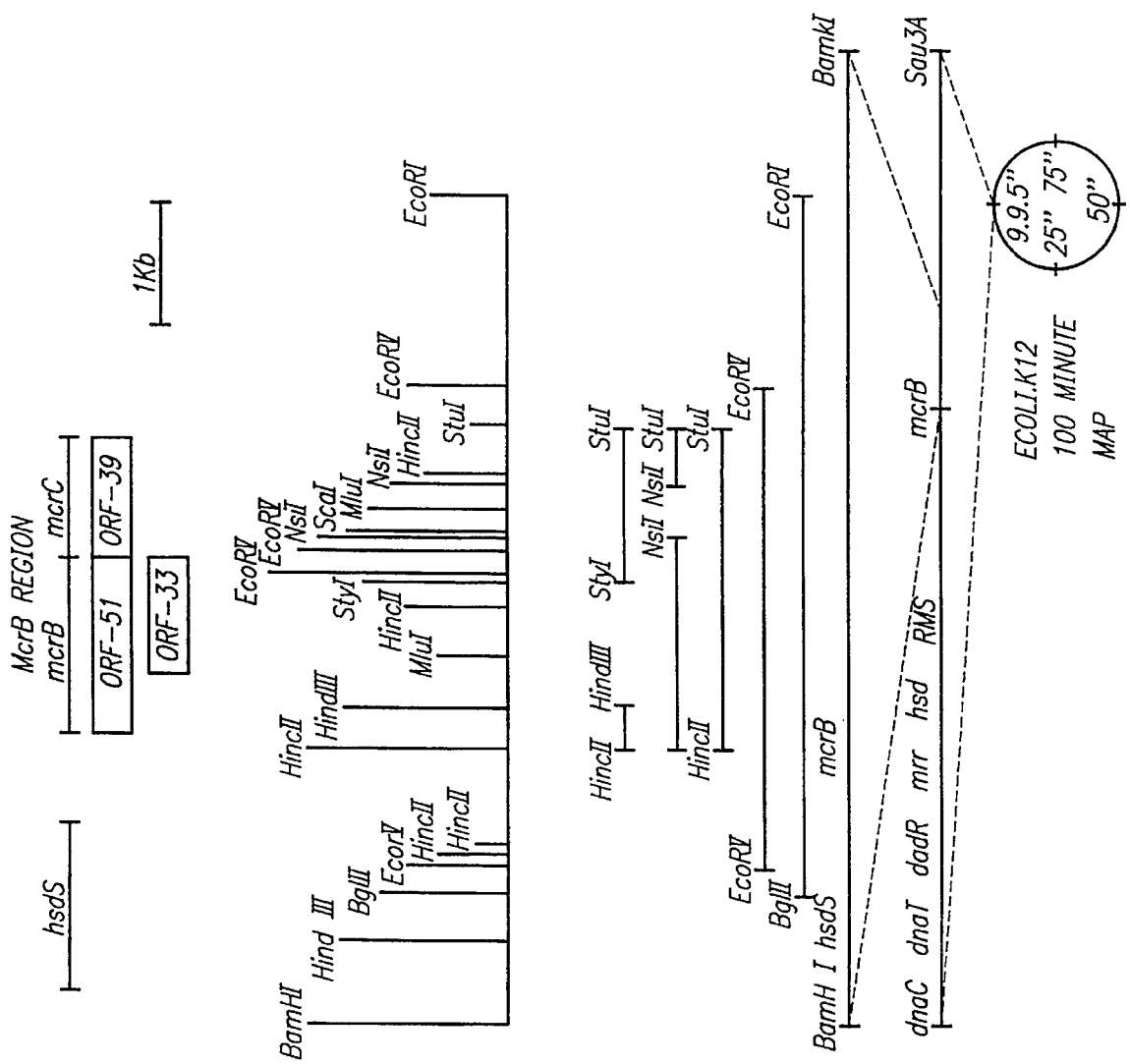

In order to determine more precisely the region of DNA responsible for the inhibition of dC-methylated lambda phase genome, the 98 minute region of E. coli K-12 LCK8 was cloned. A partial LCK8 genomic library was made in pOU61cos. (Knott, V. et al., *Nucleic Acid Res.*, 16:2601–2612 (1988)), packaged with Gigapack™ II XL (Stratagene, La Jolla, Calif.), and plated on E. coli C. Clones containing the 98 minute region were identified by colony hybridization using an oligonucleotide (ATGAGTGCGGG-GAAATTG) [SEQ ID NO: 6] probe specific to the hsd region (Gough, J. A., et al., *J. MOl. Biol.*, 166:1–19 (1983)). All clones were propagated in the host RR1-A when tested for plating efficiency of phage. As shown in FIG. 3, in panels 3A and 3B, the activity was isolated to a 2.6 kb fragment containing the mcrB gene. The mcrB region including open reading frames (Ross et al., supra) is shown in FIG. 3A. The subclones corresponding to these groups are shown directly below. The table on the far left gives information pertaining to the DNA fragment shown on the right. (The restriction map depicted in FIG. 3A and 3B, showing the location of the hsdS gene and adjacent McrB region of the E. coli K12 chromosome, is from Ross, T., et al., *J. Bact.*, 171:1974–1981 (1989).)

The results in Table 1 support the observation that the restriction activities of the minute 98 region have a negative effect on rescue efficiency. To obtain high plating efficiencies, a complete deletion of the minute 98 mcrB region (mcrB through mrr) is preferred, as opposed to a small mutation of mcrB present in most commonly used mcrB− lab strains. This is because despite the mcrB− phenotype exhibited by these mcrB− strains (using AluI methylase modified pBR322 transformation as the assay (Ross, supra,)) some inhibitory activity of the mcrB region remains. Complete deletion resulted in optimal efficiency, accounting for a greater than 1000-fold improvement in rescue efficiency using eukaryotic modified DNA.

Preferred E. coli strains for rescue of the lacZ construct from the transgenic animal genome are SCS-8 (Catalog Number 200,288) and VCS257 (Catalog Number 200,256) which are commercially available from Stratagene Cloning Systems and are also contained in a kit (Big Blue™ Mouse Mutagenesis System, Catalog Number 720,000). SCS-8 has the following genotype: recA1, endA1, mcrA, ▲(mcrBC-hsdRMS-mrr), ▲(argF-lac)U169, phi80▲lacZ▲M15, Tn10(tet$^r$). SCS-8 provides the lacZ▲M15 gene which allows for alpha-complementation when SCS-8 is infected by the packaged bacteriophage. Additional commercially available E. coli strains which contain the lacZ▲M15 genotype for use in this invention include the following: XL1-Blue (Stratagene, Catalog Number 200,236); SureTM (Stratagene, Catalog Number 200,238); PLK-F' (Stratagene, Catalog Number 200,237); JM101 (Stratagene, Catalog Number 200,234); JM109 (Stratagene, Catalog Number 200,235); and NM522 (Stratagene, Catalog Number 200, 233).

While the use of mcrB deletion strains is described herein for use in mutagenesis testing and recovery of lambda phage DNA from mammalian cells, it is apparent that restriction system deficient strains may be used for other eukaryotic DNA cloning projects.

Of course, any number or variety of test DNA sequences or genes can be inserted between lambda cos sites. The in vitro packaging extract would still excise the DNA between the cos sites and package it into a lambda phage particle. Thus, a variety of recombinant lambda genomes or cosmids may be used for this excision event.

F. Construction of Shuttle Vector Systems for Rapid DNA Sequence Identification of Mutations in Test DNA Mutations evidenced by the production of white plaques resulting from disruption of the β-galactosidase (β-gal) gene are useful for determining the mutation rate of a mutagen, but give little information regarding the specific mutation within the DNA. In addition, analysis of the specific mutation is hampered somewhat by the size of the test β-gal gene (i.e., about 3200 b.p.).

To help increase the effectiveness of the procedure, the target lambda phage can be made to provide a target gene with reduced size (e.g., the lacI gene having about 1000 b.p.), and a rapid means with which the target gene is transferred from the lambda phage into plasmid vectors for sequence analysis.

Both the lacI and β-gal genes are inserted within a lambda vector, such that if the mutation occurs within the lacI gene, the repressor activity is lost allowing the β-gal gene to be expressed giving rise to blue plaques in the absence of IPTG. In the described embodiment, the lacI gene is positioned upstream of the alpha portion of the lacZ gene in the vector (Miller, J. H. and Reznikoff, W. S., *The Operon*, 2nd Ed. Cold Spring Harbor Laboratory, 1980, pp. 104–105). When the host *E. coli* (which is infected by the bacteriophage vector) provides the complementary portion of the lacZ gene (referred to as lacZ▲M15) (Miller, J. H. and Reznikoff, W. S. supra), the gene products synthesized by these two partial genes combine to form a functional β-galactosidase protein (referred to as alpha-complementation) giving rise to blue plaques in the presence of Xgal when a mutation has occurred in the lacI gene or in the presence Xgal and IPTG when the lacI gene is not mutated. The ▲ M15 portion of the lacZ gene provided by the host is provided either episomally (via a low copy number plasmid or F-factor) or stably integrated into the bacterial chromosome. The alpha portion of lacZ is used because 1) the β-gal protein formed by alpha-complementation is known to be weaker in activity than the contiguous protein, minimizing the possibility of background blue plaques due to inefficient repression by lacI, and 2) to provide a smaller and thus more easily characterized lacZ target should this gene be used in mutagenesis studies. The requirements of the host *E. coli* in this system are the following: lacI(–), lacZ▲ M15, restriction(–). All cloning steps are outlined in the FIGS. 4 through 8 and are done using standard procedures (Sambrook, J. et al., *Molecular Cloning, A Laboratory Manual*, 2nd. Ed. Cold Spring Harbor Laboratory 1989).

The embodiment described utilizes the alpha portion of lacZ with lacI. The complete lacZ can also be used by providing a means to maintain complete repression by lacI until induction is desired. This can be done in a variety of ways including control of ▲M15 laZ expression by a lambda specific promoter (PR') which prevents lacZ expression in the host *E. coli* until several minutes following infection by the bacteriophage, allowing lacI levels to build up to suitable levels to enable complete repression. Additionally, low levels of lac repressor can be maintained in the host to assist in repression by lacI until induction occurs, either by a mutation in lacI or by addition of IPTG to the system. A third alternative is to use an altered lacI gene which gives rise to a repressor protein with higher specific activity, thereby allowing stronger repression of β-galactosidase production.

The source of starting materials for the cloning procedures are as follows: the pBluescript II SK+ and SK–, pBS(+), lambda gt11, and lambda L2B are available from Stratagene Cloning Systems, La Jolla, Calif. Lambda L47.1 and pPreB: Short, J. M., et al., *Nucleic Acids Res.*, 16:7583–7600. pMJR1560 is available from Amersham Corp., Arlington Heights, Ill.

Rapid sequencing of the mutagenized lacI gene within the lambda vector is facilitated by incorporating "lambda ZAP" excision sequence within the lambda vector. (Short, J. M. et al., *Nucleic Acids Res.*, 16:7583–7600 (1988). Lambda ZAP is a lambda phage vector which permits in vivo excision of inserts from the lambda vector to a plasmid. This is possible because the lambda phage contains the two halves of an f1 bacteriophage origin of replication. In the presence of proteins supplied by f1 helper phage, all DNA present between the two partial f1 origins is automatically excised from the lambda phage. The two halves come together to form an intact f1 origin. The resulting phagemid contains a Col E1 origin of replication and an ampicillin resistance gene, thus the insert is effectively subcloned into a plasmid vector. All sequences between the two partial f1 origins are excised as a plasmid within hours.

In the mutation analysis vector, these f1 origins are positioned so that the lacI gene can be automatically excised from the lambda phage from the mouse genomic DNA. Following this conversion from phage to plasmid, the insert may be rapidly sequenced or characterized by other known methods. Characterization of a large number of mutations within the lacI gene can be completed within 3 days following isolation of mouse genomic DNA, as opposed to several months using standard techniques.

In the example described herein, a lambda ZAP is used to convert the test DNA inserts from integration in the lambda vector to a plasmid. Other systems may also be used which allow excision and recircularization of a linear sequence of DNA thereby providing a rapid means with which the test DNA sequence may be transferred from the phage to a form suitable for analysis. Such other systems include, but are not limited to, the use of FLP-mediated (Senecoff, J. et al., *Proc. Natl. Acad. Sci. USA*, 82:7270–7274 (1985); Jayaram, M., *Proc. Natl. Acad. Sci. USA*, 82:5875–5879 (1985); McLeod, M., *Mol. Cell. Biol.*, 6:3357–3367 (1986); Lebreton, B. et al., *Genetics*, 118:393–400 (1988)) or Cre-lox site specific recombination techniques (Hoess, R. et al., *J. Mol. Biol.*, 181:351–362 (1985); Hoess, R. et al., *Proc. Natl. Acad. Sci. USA*, 81:1026–1029 (1984)).

The embodiments described above utilize the *E. coli* beta-galactosidase gene as a test DNA sequence, which allows phenotypes that are positive and negative for mutation to be observed. Other potential test DNA sequences include (but are not limited to): the lac I repressor, the cI repressor, any antibiotic resistance gene sequence (ampicillin, kanamycin, tetracycline, neomycin, chloramphenicol, etc.), the lambda red and gam gene sequences, a thymidine kinase gene sequence, a xanthine-guanine phosphoribosyl transferase gene sequence, sequences that code for restriction enzymes or methylation enzymes, a gene sequence that codes for luciferase, and/or a tRNA stop codon or frameshift suppressor gene sequence.

Figure 2:
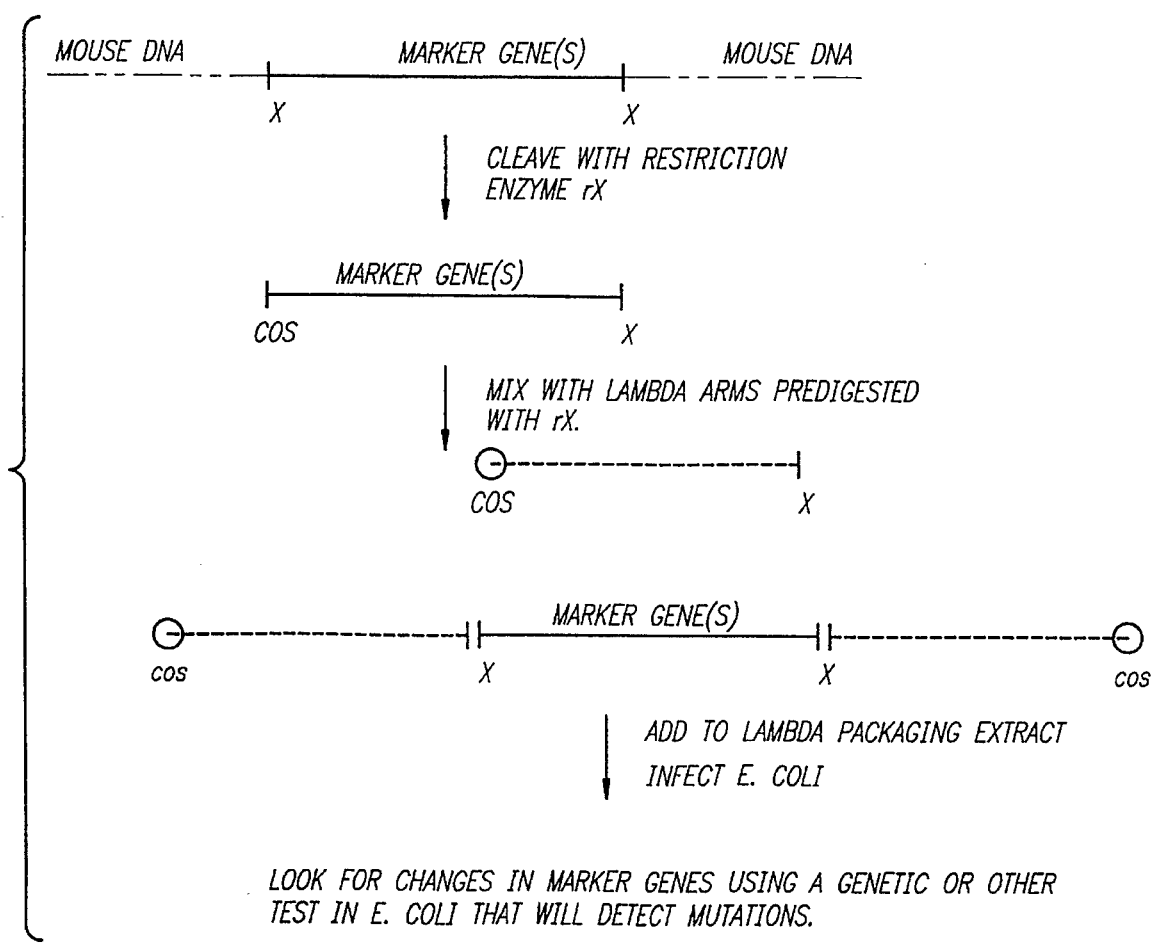

Even more general models can be made that eliminate the cos sites, although the excision mechanism now becomes different. By bracketing the test DNA sequence(s) with convenient restriction sites, as shown in FIG. 2, the test sequence(s) can be separated away from the mouse DNA with restriction enzymes and subsequently ligated with lambda or cosmid vectors which contain cos sites or if the test sequence is linked to a replication origin it can be transformed directly. Background can be reduced in such a system by including with the test DNA sequences a sequence that is necessary for lambda phage replication, which is then cloned with the test DNA sequence into a lambda genome deficient or defective in that sequence.

5. Preparation of a Modified Lambda Genome Containing a Target Gene System

The modified Lambda genome, designated Lambda LIZ alpha, is prepared through a series of molecular gene manipulations as diagrammed in FIGS. 4 through 8.

FIG. 4 depicts the construction of pBlue MI–. pBluescript SK– (Stratagene, La Jolla, Calif.) is modified using site directed mutagenesis to introduce an Ava III restriction site at a position 5' to the open reading frame for the LacI gene, but downstream from the ampicillin resistance gene and the ColE1 origin of replication present on pBluescript to form pBlue MI–.

FIG. 5 depicts the construction of pLacIq. pBluescript II SK+ (Stratagene) is digested with the restriction enzymes PstI and EcoRI, both which cleave in the polylinker region to form linearized pBluescript SK+ lacking the small fragment derived from the polylinker. pMJR1560 (Amersham Corporation, Arlington Heights, Ill.) is digested with the restriction enzymes PstI and EcoRI to release a LacIq-containing fragment that is separated by agarose gel electrophoresis and eluted from the gel. The lacIq-containing fragment is then ligated into the linearized pBluescript SK+ to form pLacIq.

Figure 6:
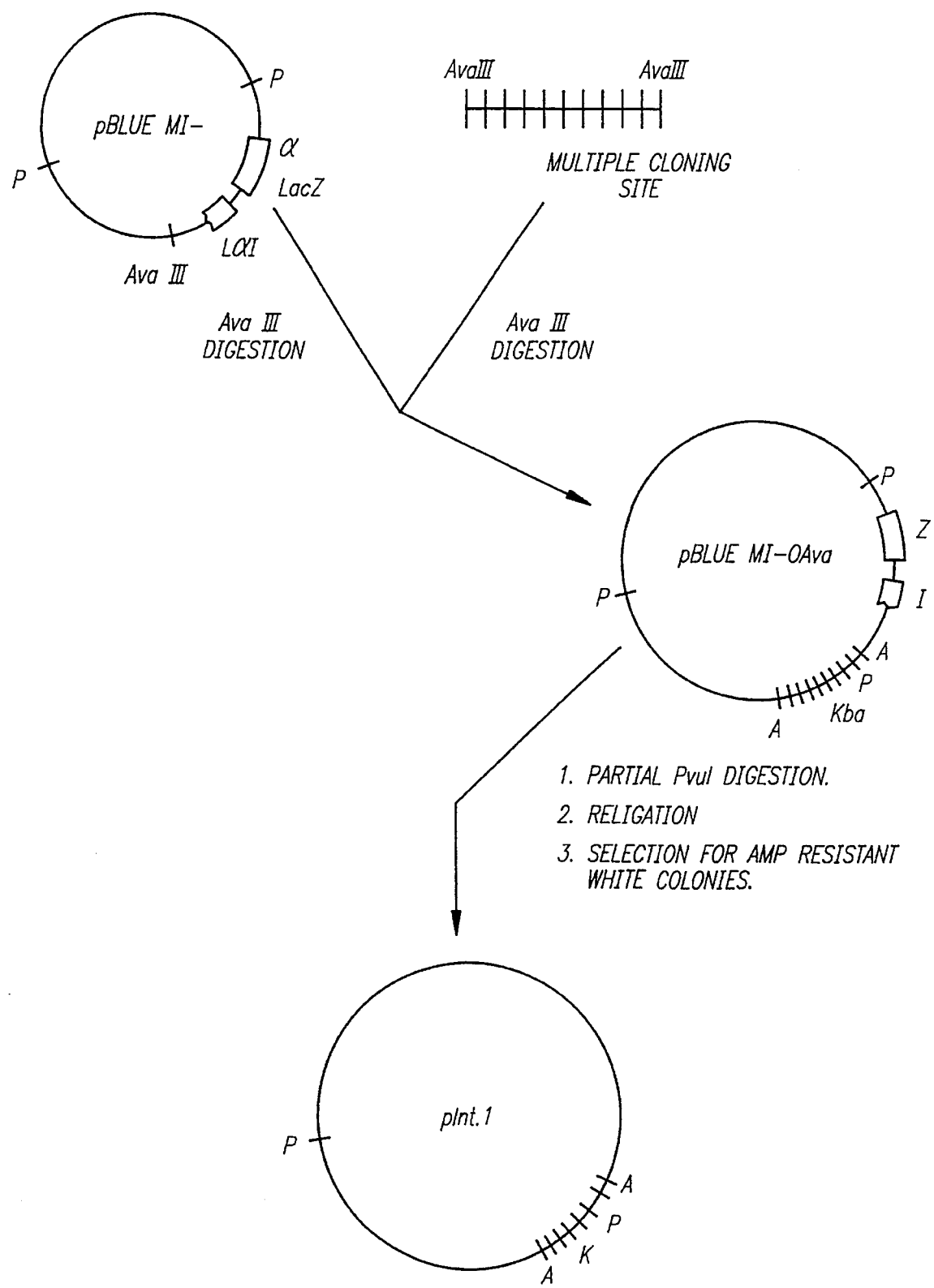

FIG. 6 depicts the construction of pInt.1. A double stranded DNA segment defining multiple cloning sites (a polylinker) is produced by synthetic oligonucleotide synthesis and annealing. The polylinker contains multiple restriction endonuclease recognition sequences including two Ava III sites flanking XbaI, KpnI and PvuI sites. The polylinker is digested with Ava III to form Ava III cohesive termini on the polylinker. pBlueMI– is digested with Ava III and the polylinker is ligated into pBlueMI–to introduce the PvuI site into the Ava III site and form pint.1

Figure 7:
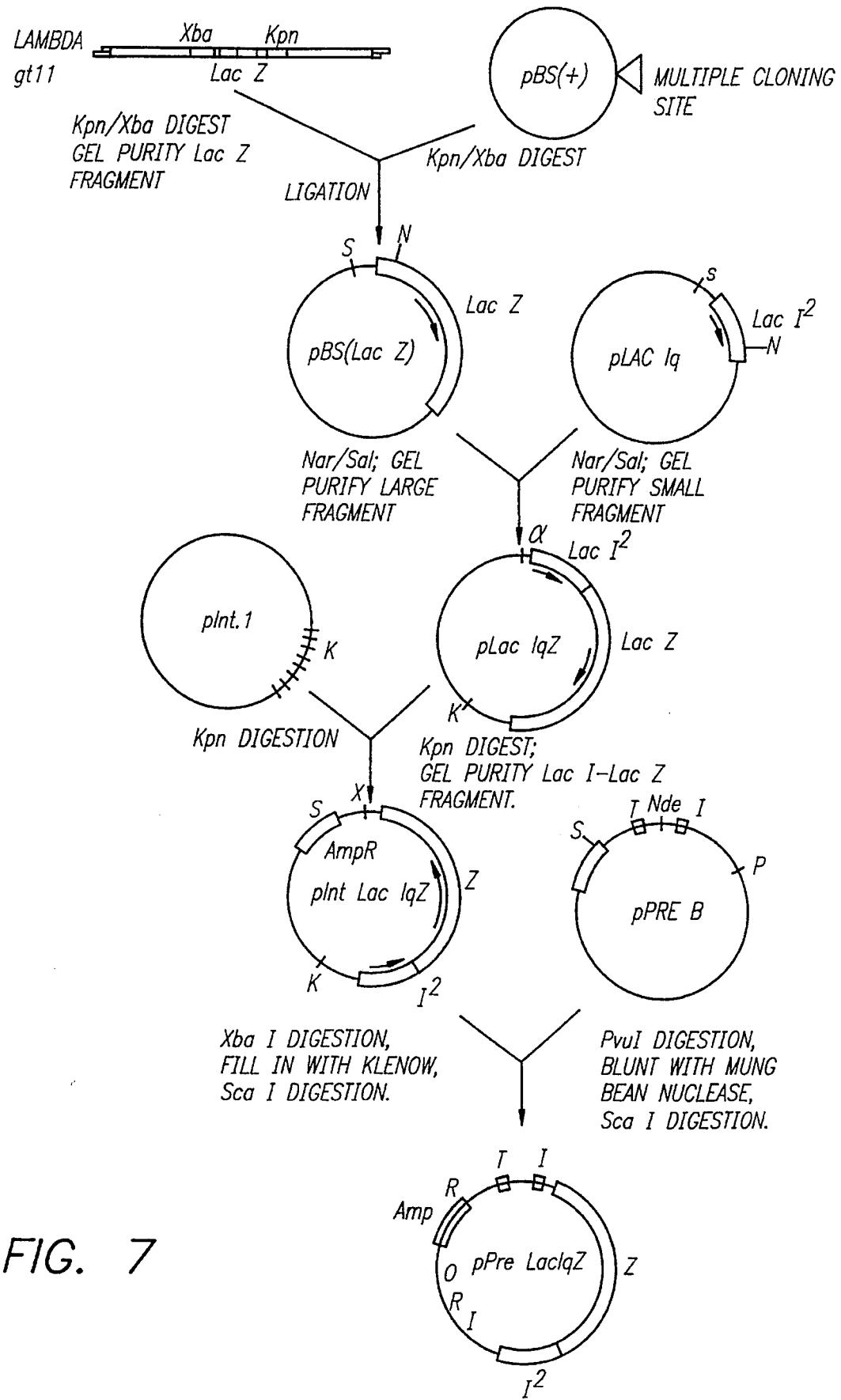

FIG. 7 depicts the construction of pPreLacIqZ (pPRIAZ). To that end, pPre B is first prepared as described by Short et al, *Nucl. Acids Res.*, 16:7583–7600 (1988).

To prepare pPre B, plasmid pUC 19 (ATCC #37254) described by Yanisch-Perron et al, *Gene*, 33:103–119 (1985), was digested with EcoRI, dephosphorylated and ligated to complementary oligonucleotides, each having compatible EcoRI ends and defining a T7 RNA polymerase promoter as described by McAllister et al, *Nucl. Acids Res.*, 8:4821–4837 (1980) to form pJF3 having the T7 promoter oriented to direct RNA synthesis towards the multiple cloning site of pUC 19. pJF3 was digested with HindIII, dephosphorylated and ligated to complementary oligonucleotides having HindIII-compatible ends and defining a T3 RNA polymerase promoter as described by Morris et al, *Gene*, 41:193–2000 (1986). A resulting plasmid, designated pBluescribe (pBS) was isolated that contained the T3 promoter oriented to direct RNA synthesis towards the multiple cloning site of pUC 19. pBS was then digested with AatII and NarI, treated with mung bean nuclease and alkaline phosphatase, and ligated to a 456 base pair (bp) RsaI/DraII blunt-end fragment isolated from the pEMBL8 plasmid described by Dente et al, *Nucl.Acids Res.*, 11:1645–1655 (1983). The 456 bp fragment contains the intergenic region of f1 phage, but does not contain the f1 gene II promoter sequence. Phagemid clones were isolated from the resulting ligation mixture and clones were isolated containing both orientations (+ or –) of the intergenic region and are designated pBS(+) or pBS(–), where "+" indicates that the intergenic region is in the same orientation as the lacZ gene. pBluescript SK(–) and SK(+) were produced from pBS(–) and pBS(+), respectively, by digestion of each with EcoRI and HindIII, followed by blunt ending with Klenow fragment of DNA polymerase I. The blunt-ended molecules were ligated to a blunt-ended synthetic polylinker containing 21 unique restriction sites as described by Short et al, *Nucl.Acids Res.*, 16:7583–7600 (1988), to form pBluescript SK(–) or SK(+), respectively. A majority of the terminator portion of the f1 intergenic region is contained on the RsaI (position 5587) to HinfI (position 5767) restriction fragment isolated from pEMBL8. The remaining terminator sequences were provided by preparing synthetic oligonucleotides as described by Short et al, supra, to provide a complete terminator, a gene II cleavage signal and unique restriction sites for EcoRV and NdeI. The synthetic oligonucleotide and the RsaI/HinfI fragment were ligated with a 3009 bp DraI/NdeI fragment obtained from pBS to form the plasmid pBST-B. The initiator domain of the f1 intergenic region was separately cloned by digesting pEMBL8 with Sau961 and DraI to form a 217 bp fragment that was then blunt-ended with Klenow and then subcloned into the NarI site of pBST-B to form pBSITO#12. pBluescript SK(–) was digested with NaeI and partially digested to cut only at the PvuI site located adjacent to the f1 origin, and the resulting fragment lacking the f1 origin was isolated. The isolated fragment was ligated to the NaeI/PvuI fragment of pBSITO#12 that contains the terminator and initiator regions of the f1 intergenic region to form plasmid pPre B.

Lambda gt11 (ATCC #37194) was digested with KpnI and XbaI to produce a 6.3 kilobase (kb) fragment containing the LacZ gene, which was agarose gel purified. pBS(+) prepared above and available from Stratagene was digested with KpnI and XbaI, and the resulting LacZ fragment was ligated into pBS(+) to form pBS(LacZ). pLacIq from above was digested with NarI and Sal I and the resulting small fragment containing the LacIq gene was isolated. pBS(LacZ) was digested with NarI and SalI and the resulting large fragment containing the LacZ gene was isolated and ligated to the small LacIq-containing fragment to form pLacIqZ. pint.1 prepared above was digested with KpnI, and the resulting linear molecule was ligated to the LacI-LacZ fragment, produced by digesting pLacIqZ prepared above with KpnI, to form pIntLacIqZ. pIntLacIqZ was then digested with XbaI, blunt-ended with Klenow, digested with ScaI, and the resulting large fragment containing LacZ-LacIq and most of the ampicillin resistance gene was isolated. pPre B prepared above was digested with PvuI, blunt ended with mung bean nuclease, digested with ScaI and the resulting fragment containing the terminator and initiator f1 intergenic region components was isolated and ligated to the pIfntLacIqZ-derived large fragment to form plasmid pPreLacIqZ (pPRIAZ)

Figure 8:
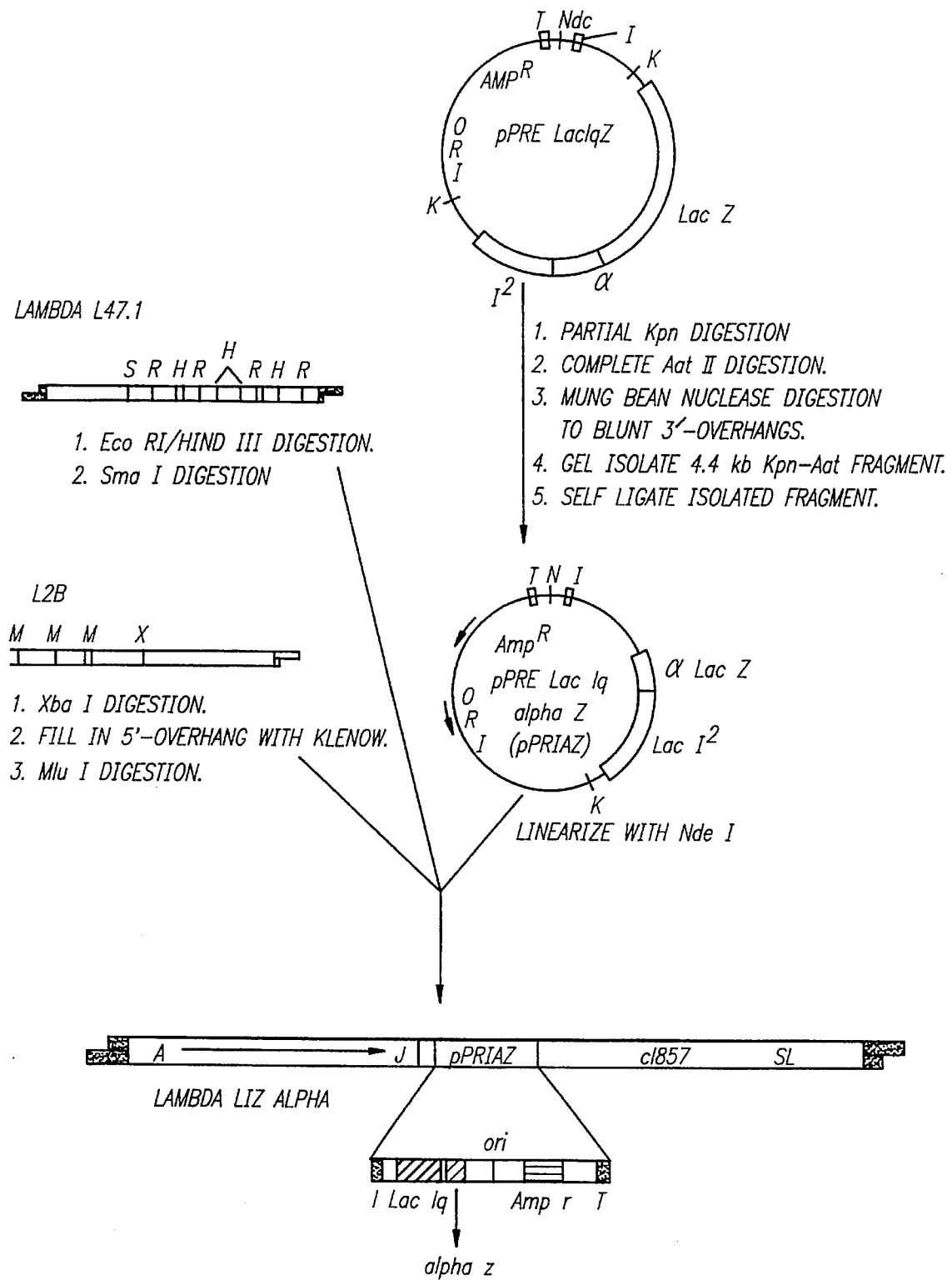

FIG. 8, depicts the construction of Lambda LIZ alpha. To that end, Lambda L47.1, described by Loenen et al, *Gene,* 10:249–259 (1980), by Maniatis et al, in "Molecular Cloning: a Laboratory Manual", at page 41, Cold Spring Harbor, N.Y. (1982), and by Short et al, supra, and having the genetic markers (srIlambdal-2)delta, imm434 cI–, NIN5, and chi A131, was digested with EcoRI, HindIII and SmaI to form a Lambda L47.1 digestion mixture. Lambda L2B, available from Stratagene, was first digested with XbaI, then treated with Klenow to fill-in the 5' XbaI overhang, then digested with MluI to form a L2B digestion mixture. The L47.1 and L2b digestion mixtures were ethanol-precipitated to prepare the DNA for ligation, and were then ligated to pPRIAZ prepared above that had been linearized with NdeI to form Lambda LIZ alpha.

The final construction, Lambda LIZ alpha, is a preferred modified Lambda bacteriophage for use in the present invention because it combines the elements of 1) a reporter gene in the form of the alpha component of LacZ, 2) the lambda bacteriophage excision capability provided by the presence of the cos sites at the termini, 3) an indicator gene system in the form of the LacIq target gene, including a lacI promoter and the repressor structural gene sequences, and 4) an f1 origin of replication arranged according to the in vivo excision system of Short et al, supra, that allows quick isolation of the mutated test gene from positive colonies containing the mutated test gene for sequencing.

6. Production of Chimeric SCID/hu Mice

A. Preparation of Human Lymphocytes

Peripheral blood lymphocytes (PBLs) are isolated from venous blood drawn from volunteer donors. First, one hundred milliliters (ml) of blood are anticoagulated with a mixture of 0.14 M citric acid, 0.2M trisodium citrate, and 0.22M dextrose. The treated blood is layered on Histopaque-1077 (Sigma, St. Louis, Mo.) to form isolated PBLS which are recovered by centrifugation at 400×g for 30 minutes at 25° C. Isolated PBLs are then washed twice with phosphate buffered saline (PBS) (150 mM sodium chloride and 150 mM sodium phosphate, pH 7.2 at 25° C.). The resulting PBL cell pellet is resuspended in PBS to a concentration of $1 \times 10^8$ cells/ml.

Lymphocytes are also isolated from tonsils obtained from therapeutic tonsillectomies from consenting patients. The tonsils are first homogenized and then lymphocytes are isolated over Histopaque as described above.

Subject rDNA are then inserted into the isolated lymphocytes using techniques known to one skilled in the art. Preferred techniques are electroporation of lymphocytes and calcium chloride permeabilization of the lymphocytes.

B. Preparation of SCID Mice

SCID mice having the autosomal recessive mouse mutations scid are obtained from Imdyme (San Diego, Calif.). Alternatively, SCID mice are derived from an inbred strain of mice, C.B-17 (Balb/c-C57BL/Ka-Igh-1b/ICR (N17F34) as described by Bosma et al., *Nature,* 301:527–530 (1983). Analysis of the pedigree of mice lacking IgM, IgG1 or IgG2a determined that the defect was inheritable and under the control of the recessive scid gene. Bosma et al., supra. A colony of mice can be established which are homozygous for the defective gene. The SCID mice are maintained in microisolator cages (Lab Products, Maywood, N.J.) containing sterilized food and water.

C. Preparation of SCID/hu Chimeras

SCID mice obtained in Example 6b are reconstituted by intraperitoneal injection with at least $5 \times 10^7$ human PBLs or tonsil lymphocytes prepared in Example 6a. The recipient SCID mice are designated SCID/hu chimeras which contain the subject rDNA. The human PBL reconstituted SCID mouse model is then used for assaying the effects of mutagens on human cells as described in this invention.

7. Preparation of a Prolysogenic Microorganism

A prolysogenic microorganism (a prolysogen) was prepared as described below, and was used as exemplary of the methods of this invention. The prolysogen was constructed in *E. coli* strain SCS-8 available from Stratagene (La Jolla, Calif.) using the procedures of Herrero et al, *J. Bacteriol.,* 172:6557–6567 (1990), to introduce a stably integrated copy of the lambda cI gene into the genome, and form the *E. coli* designated SCS-8cI. The genotype of *E. coli* strain SCS-8 has been described in some detail by Kohler et al, *Proc.Natl.Acad.Sci.USA,* 88:7958–7962 (1991). SCS-8 is resistant to the antibiotic tetracycline.

The prolysogen *E. coli* strain SCS-8cI has been deposited with the American Tissue Culture Collection (ATCC; Rockville, Md.) on Feb. 14, 1992, and has been assigned an ATCC accession number 55297.

For the construction of SCS-8cI, the plasmid pUC18Sfi I was first prepared as described by Herrero et al, supra. pUC18Sfi I was derived from pUC18 by adding two Sfi I restriction sites flanking the polylinker. Two oligonucleotide primers were synthesized that correspond to the termini of the wild type cI gene nucleotide sequence described in "Lambda II" by Hendrix et al, at page 631. These two primers (p1 and p2) were designed for use as PCR primers to amplify a cI gene-containing fragment when used on wild type lambda in the form of a *E.coli* lysogen extract of strain N99. The primers have the nucleotide sequences as follows:

p1   5'-ATCAGCGAATTCCAACCTCCTTAGTA-CATGCAA-3', [SEQ ID NO:7] and p2   5'-CATACGGTCGACGATCAGC-CAAACGTCTCTTCAGG-3', [SEQ ID NO: 8].

p1 includes to nucleotides 38019 to 38039 of lambda, and p2 includes nucleotides 37225 to 37255 of lambda. The resulting PCR product was inserted into the polylinker region of the plasmid pUC18Sfi I, and then removed from the plasmid by digestion with Sfi I, to form a PCR fragment having Sfi I cohesive termini. The plasmid pUTKm described and available from Herrero et al, *J.Bacteriol.,* 172:6557–6567 (1990), was digested with Sfi I, and the PCR fragment was ligated into pUTKm to form plasmid pUTKm-cI. pUTKm contains the 19 base pair ends of the transposon Tn5 required for insertion of DNA fragments into genomic DNA. Between the flanking ends, termed insertion elements, in a selectable marker, the gene for kanamycin resistance (kan), and a restriction endonuclease site for Sfi I into which the PCR fragment containing the cI gene was ligated. Outside the insertion elements is the tnp gene encoding the transposase protein required for the transposition function. Thus, upon transposition, the tnp gene is left behind, so that the genomically integrated insertion fragment having the cI and kan genes cannot be excised by transposition in the absence of a transposase protein.

Plasmid pUTKm also contains an R6K origin of replication (ori) that requires the pir gene product for replication. pUTKm was propagated in the S17-1 *E.coli* strain that contains the pir gene (pir$^+$) also described and provided by Herrero et al, supra. S17-1 is sensitive to both of the antibiotics kanamycin and tetracycline.

Plasmid pUTKm-cI was transformed into *E.coli* S17-1 according to standard bacterial transformation methods, and cultured in kanamycin to select for transformants containing the plasmid, and were designated s17-1/pUTKm-cI.

For production of a stable integration of the cI gene in pUTKm-cI into the genome of the SCS-8 strain of *E.coli,* a standard mating protocol was conducted where cultures of SCS-8 and s17-1/pUTKm-cI were coincubated together. Plasmid pUTKm-cI was transferred by conjugation to SCS-8 cells, and the resulting conjugants were plated onto plates containing kanamycin and tetracycline. The tetracycline kills the S17-1 cells, leaving only the SCS-8 cells, which are tet$^R$. The absence of the pir gene product in the SCS-8 cells prevents the plasmid pUTKm-cI from replicating, thereby providing the selective pressure for transposition to occur in order to maintain the kanamycin gene in the E.coli cells. The resulting viable cells are SCS-8 E.coli containing integrated cI by transposition, and having antibiotic resistance to both kanamycin and tetracycline at 50 and 15 ug/ml, respectively. These viable cells are designated SCS-8cI cells, and are exemplary herein as a prolysogenic microorganism because the expression of the cI gene product prevents the cell for entering the lytic phase upon infection by a lysis-competent lambda bacteriophage.

8. In Vivo Mutagenesis Testing Assay Using a Prolysogen

The previous examples described in vivo mutagenesis assays using either a Lac Z or Lac I target gene within a lambda shuttle vector. In that assay, genomic DNA from a transgenic mouse was exposed to in vitro lambda packaging extract which allows lambda phage genomes containing the Lac Z or Lac I target gene to be recovered from the mouse genome. The resulting phage particles were then adsorbed to an E. coli host and plated with top agar on rich NZY media. Incubation of the plates allowed the formation of plaques which were then scored according to color. When a "phenotypic" mutation was present in the Lac I gene, for example, the Lac repressor is no longer able to block expression of the alpha-Lac Z gene that is present in the recovered phage genome. This alpha-Lac Z protein is then able to complement with the omega-Lac Z protein that is produced constitutively in the host E.coli strain to form a functional beta-galactosidase protein. This protein then breaks down the chromogenic substrate, X-gal, that is present in the top agar media of the plate. As the phage genome replicates in the E.coli cells, a blue plaque will form indicating the presence of a mutant LacI target gene. If a non-mutant Lac I target is present, a colorless plaque will form.

Because both mutant and non-mutant targets are scored in this assay, it is considered a non-selectable system for screening for mutagenesis of the target gene. Although this system generated easily identifiable mutants, plating densities cannot exceed 50,000 plaques per 25×25 cm plate and are optimal at densities of 25,000 plaques per plate. Based on these numbers, 10–20 plates are required for each mouse tissue analyzed. The number of plates contributes significantly to the cost of the assay in terms of plates, media, X-gal substrate and labor. The system described in this example is a selectable, and preferred, version of this assay in which only phage that harbor mutant Lac I target genes can survive and be identified on the plate. This selection allows a higher plating density to be used: up to 500,000 phage and thus 500,000 target genes, can be screened on one 25×25 cm plate, significantly decreasing the cost and time to perform the assay.

The identification of mutants using the present selectable system depends on the expression of the alpha-lacZ gene to create a functional beta-galactosidase protein. This protein allows the cell to utilize lactose for growth. Thus, cells carrying phenotypically mutant lacI genes can grow on minimal media containing lactose as the sole carbon source. Cells carrying non-mutant lacI genes code for a functional Lac repressor and therefore cannot express alpha-lacZ, and die from carbon starvation. Thus the system is selectable for only those target genes which have been mutagenized, thereby inactivating the lacI gene.

The plating media required for this selection consists of the following components expressed per liter and are obtained from Sigma Chemical Co. (St. Louis, Mo.) unless noted differently: 6.0 g Na$_2$HPO$_4$, 1.0 g NH$_4$Cl, 0.5 g NaCl, 20.0 g Bacto Agar, 0.5 g lactose, 0.34 g thiamine HCl, 1.10 ml of 1M MgsO$_4$, 0.1 ml of 1M CaCl$_2$. The top agar consists of the following components expressed per liter: 6.0 g Na$_2$HPO$_4$, 3.0 g KH$_2$PO$_4$, 1.0 g NH$_4$Cl, 0.5 g NaCl, 3.5 g Seakem Agarose (FMC, Rockland, Me.), 0.4 g Difco casamino acids, 2.0 g X0gal (Stratagene Cloning Systems, La Jolla, Calif.). Note that X-gal was used in this media not to allow distinction between mutants and non-mutants but to allow easier identification of the mutants on the light colored minimal media plates.

Variations in the media formulation can be utilized, however, it was determined that lactose should not be included in the top agar, as this contributed to elevated levels of false positive bacterial cell growth (higher backgrounds). In addition, the rate of growth for the lactose-dependent cells was improved when casamino acids were included in the top agar.

In addition to the change in media that is required for the selectable system to function, a new E. coli strain was also required. Because the selection depends on survival of the host cells as opposed to plaque formation, it is necessary to inhibit lytic growth of the rescued phage particles once they have adsorbed to the host E. coli cells. This was done by using a strain of E. coli that carries the lambda cI gene, which strain being referred to herein as a prolysogenic strain because it maintains the lambda infection in a non-lytic life cycle. The cI gene specifies the lambda repressor protein which allows lambda genomes to be maintained in the lysogenic state as opposed to replicating lytically. In the strain used in this system, SCS-8cI, the cI gene is stably integrated in the E. coli chromosome as described above.

E. coli strain SCS8-cI and the minimal media described above are the two major changes that are incorporated into the protocol described in the earlier Examples 1–6 for the non-selectable version of mutagenesis testing assay of this invention. The general method of the assay was as follows: First, genomic DNA was isolated from transgenic mouse tissue. Approximately 20.0 ul of the DNA was then packaged using Transpack in vitro lambda packaging extract (produced as described earlier) for three hours at 30° C. SM buffer was then added to the reaction tube to give a final volume of one ml. Fifty ul of the reaction was then plated according to the protocol described for the previous non-selectable system. The remaining 900 ul of the packaging reaction was then adsorbed to SCS-8cI cells (prepared as previously described with the exception that the cells are resuspended to an OD of 2.0 after spinning), for 20 minutes at 30° C. followed by mixing with 2.5 ml of minimal top agar and pouring onto a 25×25 cm plate containing lactose minimal media. This plate was then incubated for approximately 60 hours at 30° C. before scoring the blue mutant colonies. The non-selectable plate was scored for total number of plaques to determine the rescue efficiency as previously described. Note that in this system one packaging reaction was used to set-up two plates: one non-selectable plate that allows determination of rescue efficiency and one selectable plate that allows ~500,000 plaques to be scored for the presence of mutant lacI target genes. In the non-selectable system, ~10~12 plates would be required to screen the same number of targets.

In initial experiments to test the frequency of mutagenic events in a target (test) DNA gene (also referred to as a bioassay) using this selectable system, several different stocks of mutant lacI phage particles (phage having known defects in lacI) were used to determine the rate of lysogenization obtainable with each particular mutant. The phage were adsorbed to SCS-8cI and plated in top agar on the selective minimal media described above. The plates were incubated at 30° C. for 60 hours after which time the total number of colony forming units (cfu) was determined. A second plate was set up using the same number of phage particles used for the first plate, however in this case SCS-8 was the E. coli host and the non-selectable rich NZY media was used. Following incubation at 37° C. for ~18 hours the total number of plaque forming units (pfu) was determined. The total number of cfu was divided by the total number of pfu to give the rate of lysogenization. A similar test was done using a wildtype lacI phage stock. As shown in Table 2, this selectable system allows very high rates of lysogenization. The data also shows that cells carrying a lysogenized phage with a mutant lacI gene are able to form colonies on this media while those cells carrying phage with non-mutant lacI genes are not able to form colonies. Thus the lysogenization/selection system functions extremely efficiently.

TABLE 2

| lacI Phage Stock | Lysogenization Rates | | |
| --- | --- | --- | --- |
|  | cfu | pfu | Rate |
| Mutant A1 | 71 | 68 | 104% |
| Mutant D9 | 425 | 421 | 101% |
| Mutant D10 | 60 | 83 | 75% |
| Wildtype | 0 | 80 | (Not tested) |

Figure 9:
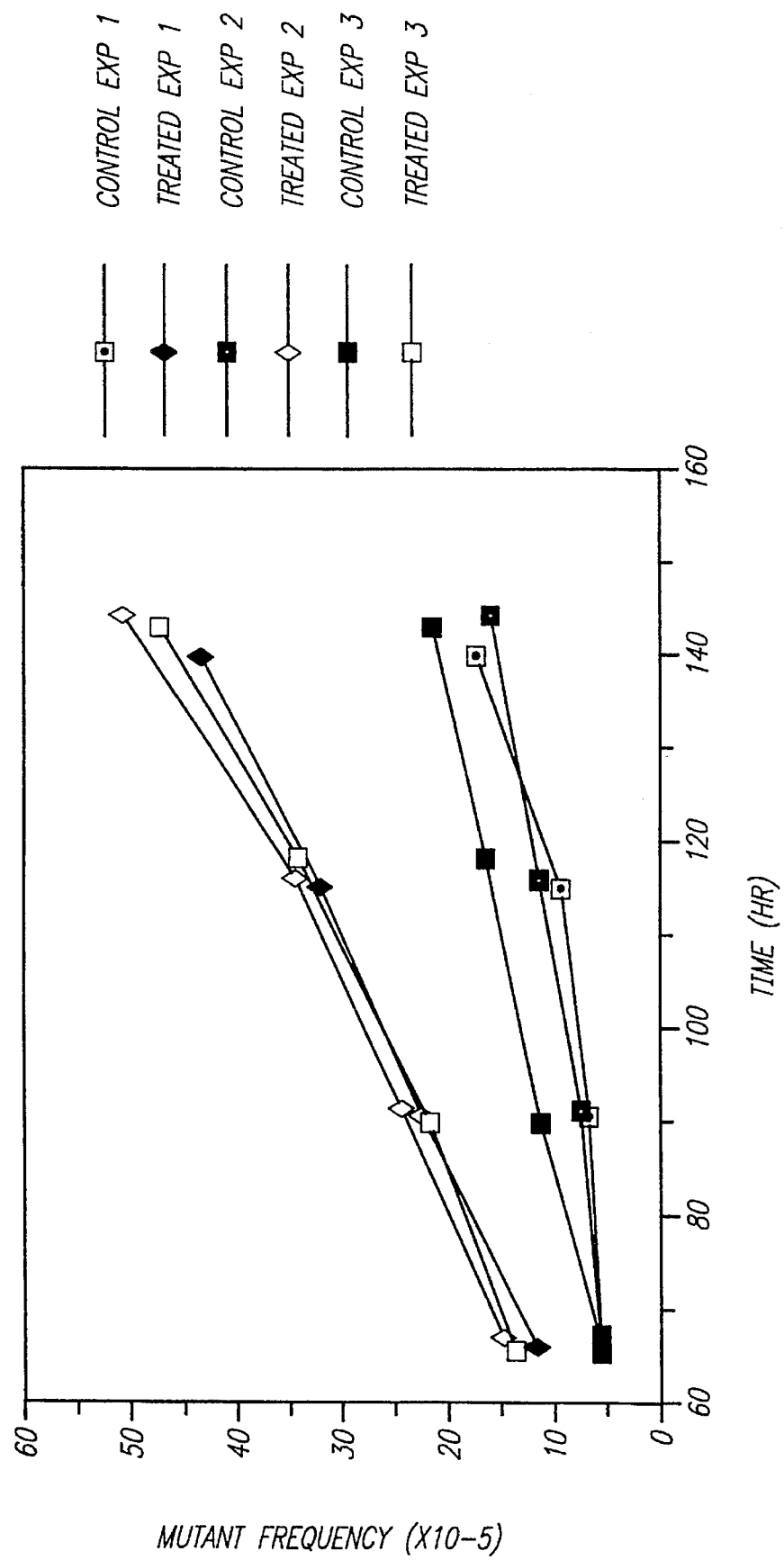

The selectable system was then evaluated for its ability to detect both spontaneous and induced mutant lacI targets rescued from the mouse genome. Following a standard dosing regimen to treat mice with methylnitrosylurea (MNU), genomic DNa was prepared from the liver of animals treated as described in previous assays, as well as from untreated control animals. The selectable mouse mutagenesis assay was then performed on three separate days (experiments 1, 2, 3) as described above. The results are shown in FIG. 9 as mutant frequency versus time. The mutation frequency is the number of mutant colonies obtained divided by the total number of phage particles screened as calculated from the non-selectable plate. The time represents the hours at which the mutant colonies were counted after being placed in the 30° C. incubator. The data show that both spontaneous and induced mutant lacI targets can be detected with this selectable assay allowing the calculation of mutant frequencies. The data also demonstrates the reproducibility of the assay as determined by three independent experiments. Additionally, induction rates can be detected with this system as seen by the increased number of mutants observed with the treated (induced) DNa relative to the untreated (control) DNA.

The data in FIG. 9 is expressed over time because mutants continue to arise overtime. It is possible that a correlation exists between the time that a mutant colony appears and the specific type of mutation that is present in the lacI gene. This may aid in classifying the mutants. For example, a colony that appears early may contain a "strong" mutation while a colony that appears late may contain a "weak" mutation that confers more of a "leaky" LacZ phenotype.

The selectable system described above is flexible in that the components and concentrations of the components of the minimal media may be varied as can the incubation temperature of the plates. These changes can effect the growth rate of the cells and thus alter the time at which the plates can be scored.

Thus, the selectable version of the previously described mouse mutagenesis assay can be used to determine mutation frequencies and induction rates. In order for this selectable system to function, two major modifications to the original assay were required: the new E. coli strain (designated as a prolysogen) was constructed, and a different plating media was developed. This system allows ~10-20 fewer plates to be used, thus significantly reducing the cost of the assay in terms of plates, media, X-gal chromogenic substrate, and labor. In addition, the selectable system allows the classification of lacI mutants and permits a wider and/or different spectrum of mutants to be detected.

The foregoing is intended as illustrative of the present invention but not limiting. Numerous variations and modifications can be effected without departing from the true spirit and scope of the invention.

What is claimed is:

1. A mutagenesis testing method comprising:
   (a) exposing a transgenic mouse to a test agent, said transgenic mouse comprising somatic and germ cells containing a test DNA sequence recoverable from said cells via enzymatic excision sites, the expression of said sequence being capable of detection in bacteria by bioassay, wherein said bioassay selects for cells containing mutations in said test DNA sequence, wherein said test sequence is selected from the group consisting of LacZ, LacZα, LacI and LacI$^Q$;
   (b) recovering a sample of said test DNA sequence from said exposed mouse, wherein said recovery is mediated through enzymatic excision of a type functional for lambda cos sites or lambda ZAP excision sites; and
   (c) determining by bioassay in a prolysogenic $E.\ coli$ that is restriction system deficient the frequency of mutation of said test DNA sequence in said recovered sample.

2. The method in accordance with claim 1 wherein said determining of step (c) comprises:
   (d) treating said recovered sample of step (b) with a restriction endonuclease to form ligatable termini flanking said test DNA sequence;
   (e) circularizing said test DNA sequence via said ligatable termini;
   (f) transforming said prolysogenic restriction system deficient $E.\ coli$ of step (c) with said circularized target DNA sequences of step (e).

3. The method in accordance with claim 1 wherein said test DNA sequence includes LacI or LacI$^q$.

4. The method in accordance with claim 3 wherein said test DNA sequence includes LacZα.

5. The method in accordance with claim 1 wherein said recovering of step (b) comprises rescue of the test DNA sequence by admixture of a sample of test DNA sequence from said exposed mouse with a lambda phage packaging extract to form lambda phage packaged test DNA sequence.

6. The method in accordance with claim 5 wherein said lambda phage packaging extract is deficient in at least one of the restriction systems mcrA, mcrB, mrr and hsdR.

7. A mutagenesis testing method comprising:
   (a) exposing a transgenic mouse to a test agent, said transgenic mouse comprising somatic and germ cells containing a test DNA sequence recoverable from said cells via enzymatic excision sites, the expression of said sequence being capable of detection in bacteria by bioassay, wherein said bioassay selects for cells containing mutations in said test DNA sequence, wherein said test sequence is selected from the group consisting of LacZ, LacZα, LacI and LacI$^Q$;
   (b) recovering a sample of said test DNA sequence from said exposed mouse, wherein said recovery is mediated through enzymatic excision of a type functional for lambda cos sites or lambda ZAP excision sites;
   (c) treating said recovered sample of step (b) with a restriction system deficient bacteriophage packaging extract to package said recovered test DNA sequence of step (b);
   (d) infecting a phage-free, prolysogenic strain of $E.\ coli$ with said packaged test DNA sequence; and
   (e) determining by bioassay of said infected $E.\ coli$ of step (d) the frequency of mutation of said test DNA sequence.

8. A mutagenesis testing method comprising:
   (a) exposing a transgenic mouse to a test agent, said transgenic mouse comprising somatic and germ cells containing a test DNA sequence contained within a system permitting enzymatic excision and circularization of the test DNA sequence, wherein said test sequence is selected from the group consisting of LacZ, LacZα, LacI and LacI$^Q$;
   (b) recovering a sample of said test DNA sequence from said exposed mouse, wherein said recovery is mediated through enzymatic excision of a type functional for lambda cos sites or lambda ZAP excision sites; and
   (c) determining by bioassay in a prolysogenic $E.\ coli$ that is restriction system deficient the frequency of mutation of said test DNA sequence in said recovered sample, wherein said bioassay selects for cells containing mutations in said test DNA sequence.

9. The mutagenesis testing method of claim 8 wherein said excision and circularization system is lambda ZAP.

10. The mutagenesis testing method of claim 8 wherein said excision and circularization system is Cre-lox site-specific recombination.

11. A mutagenesis testing method comprising:
    (a) exposing a transgenic mouse to a test agent, said transgenic mouse comprising somatic and germ cells containing a test DNA sequence contained within a system permitting enzymatic excision and circularization of the test DNA sequence, wherein said test sequence is selected from the group consisting of LacZ, LacZα, LacI and LacI$^Q$;

(b) recovering a sample of said target DNA sequence within said system from said exposed mouse, wherein said recovery is mediated throuqh enzymatic excision of a type functional for lambda cos sites or lambda ZAP excision sites;

(c) excising and circularizing the test DNA sequence in said recovered sample using said system; and d) determining by bioassay in a phage-free prolysogenic strain of *E. coli* that is restriction system deficient the frequency of mutation of said test DNA sequence in said circularized sample, wherein said bioassay selects for cells containing mutations in said test DNA sequence.

12. A mutagenesis testing method comprising:

(a) exposing a transgenic mouse to a test agent, said transgenic mouse comprising somatic and germ cells containing a test DNA sequence flanked on both sides by one of two halves of an f1 bacteriophage origin of replication contained by a bacteriophage origin of replication contained by a bacteriophage derivative genome, wherein said test sequence is selected from the group consisting of LacZ, LacZ$\alpha$, LacI and LacI$^Q$;

(b) rescuing with f1 helper phage proteins a sample of said test DNA sequence from said exposed mouse; and (c) determining the frequency of mutation of said test DNA sequence in said rescued sample by bioassay in a prolysogenic *E. coli* that is restriction system deficient, wherein said bioassay selects for cells containing mutations in said test DNA sequence.

13. A mutagenesis testing method comprising:

(a) exposing a transgenic mouse to a test agent, said transgenic mouse comprising somatic and germ cells containing a test DNA sequence flanked on both sides by one of two halves of an f1 bacteriophage origin of replication contained by a bacteriophage origin of replication contained by a bacteriophage derivative genome, wherein said test sequence is selected from the group consisting of Lacz LacZ$\alpha$, LacI and LaCI$^Q$;

(b) recovering a sample of said test DNA sequence from said exposed mouse;

(c) excising a sample of the recovered test DNA sequence with f1 helper phage proteins;

(d) determining the frequency of mutation of said test DNA sequence in said excised sample by bioassay in a prolysogenic *E. coli* that is restriction system deficient, wherein said bioassay selects for cells containing mutations in said test DNA sequence.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

TGTGGAATTG TGAGCGCTCA CAATTCCACA                                               30

( 2 ) INFORMATION FOR SEQ ID NO:2:

( i ) SEQUENCE CHARACTERISTICS:

(A) LENGTH: 18 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:2:

ATTGTGAGCG CTCACAAT 18

(2) INFORMATION FOR SEQ ID NO:3:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:3:

GGAATTGTGA GCGGATAACA ATCC 24

(2) INFORMATION FOR SEQ ID NO:4:

(i) SEQUENCE CHARACTERISTICS:
(A) LENGTH: 13 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:4:

AACNNNNNNG TGC 13

(2) INFORMATION FOR SEQ ID NO:5:

(i) SEQUENCE CHARACTERISTICS:
(A) LENGTH: 13 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:5:

GCACNNNNNN GTT 13

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:6:

ATGAGTGCGG GGAAATTG 18

(2) INFORMATION FOR SEQ ID NO:7:

(i) SEQUENCE CHARACTERISTICS:
(A) LENGTH: 33 base pairs
(B) TYPE: nucleic acid
(C) STRANDEDNESS: unknown
(D) TOPOLOGY: unknown ( i i ) MOLECULE TYPE: DNA (genomic)

( x i ) SEQUENCE DESCRIPTION: SEQ ID NO:7:

ATCAGCGAAT TCCAACCTCC TTAGTACATG CAA 33

( 2 ) INFORMATION FOR SEQ ID NO:8:

( i ) SEQUENCE CHARACTERISTICS:
      ( A ) LENGTH: 35 base pairs
      ( B ) TYPE: nucleic acid
      ( C ) STRANDEDNESS: unknown
      ( D ) TOPOLOGY: unknown ( i i ) MOLECULE TYPE: DNA (genomic)

( x i ) SEQUENCE DESCRIPTION: SEQ ID NO:8:

CATACGGTCG ACGATCAGCC AAACGTCTCT TCAGG 35